US009801907B2

(12) United States Patent
Piene

(10) Patent No.: US 9,801,907 B2
(45) Date of Patent: *Oct. 31, 2017

(54) FILM-COATED AND/OR GRANULATED CALCIUM-CONTAINING COMPOUNDS AND USE THEROF IN PHARMACEUTICAL COMPOSITIONS

(71) Applicant: Takeda Nycomed AS, Asker (NO)

(72) Inventor: Jan Yngvar Piene, Asker (NO)

(73) Assignee: Takeda AS, Asker (NO)

( * ) Notice: Subject to any disclaimer, the term of this patent is extended or adjusted under 35 U.S.C. 154(b) by 141 days.

This patent is subject to a terminal disclaimer.

(21) Appl. No.: 14/472,441

(22) Filed: Aug. 29, 2014

(65) Prior Publication Data

US 2015/0050353 A1   Feb. 19, 2015

Related U.S. Application Data

(63) Continuation of application No. 12/085,799, filed as application No. PCT/DK2006/000696 on Dec. 7, 2006, now Pat. No. 8,846,101.

(60) Provisional application No. 60/850,130, filed on Oct. 6, 2006.

(30) Foreign Application Priority Data

Dec. 7, 2005  (DK) ................................ 2005 01736
Sep. 15, 2006 (DK) ................................ 2006 01203

(51) Int. Cl.
| | |
|---|---|
| A61K 33/10 | (2006.01) |
| A61K 9/00 | (2006.01) |
| A61K 9/20 | (2006.01) |
| A61K 33/06 | (2006.01) |
| A61K 9/16 | (2006.01) |
| A23L 29/30 | (2016.01) |
| A23L 33/15 | (2016.01) |
| A23L 33/16 | (2016.01) |

(52) U.S. Cl.
CPC .............. *A61K 33/10* (2013.01); *A23L 29/37* (2016.08); *A23L 33/15* (2016.08); *A23L 33/16* (2016.08); *A61K 9/0056* (2013.01); *A61K 9/0095* (2013.01); *A61K 9/1623* (2013.01); *A61K 9/1635* (2013.01); *A61K 9/1694* (2013.01); *A61K 9/2018* (2013.01); *A61K 9/2027* (2013.01); *A61K 9/2077* (2013.01); *A61K 33/06* (2013.01); *A23V 2002/00* (2013.01); *A61K 9/2009* (2013.01); *A61K 9/2013* (2013.01); *Y10T 428/31844* (2015.04); *Y10T 428/31971* (2015.04)

(58) Field of Classification Search
None
See application file for complete search history.

(56) References Cited

U.S. PATENT DOCUMENTS

| | | |
|---|---|---|
| 4,051,243 A | 9/1977 | Seubert et al. |
| 4,162,319 A | 7/1979 | Seubert et al. |
| 4,664,915 A | 5/1987 | Simonian |
| 4,684,534 A | 8/1987 | Valentine |
| 4,830,859 A | 5/1989 | Finnan et al. |
| 5,108,728 A | 4/1992 | Rau et al. |
| 5,198,227 A | 3/1993 | Batista et al. |
| 5,846,506 A | 12/1998 | Esch et al. |
| 6,149,941 A | 11/2000 | Schwarz et al. |
| 6,355,271 B1 | 3/2002 | Bell et al. |
| 6,475,510 B1 | 11/2002 | Venkatesh et al. |
| 6,716,454 B2 | 4/2004 | Meignant et al. |
| 7,198,653 B2 | 4/2007 | Lang et al. |
| 7,638,143 B2 * | 12/2009 | Piene .................... A61K 9/0007 424/602 |
| 8,007,752 B2 * | 8/2011 | Piene .................... A61K 9/0007 423/305 |
| 2002/0090419 A1 | 7/2002 | Rothlin |
| 2003/0069213 A1 | 4/2003 | Il et al. |
| 2003/0211168 A1 | 11/2003 | Lynenskjold et al. |
| 2004/0071772 A1 | 4/2004 | Narita et al. |
| 2004/0121006 A1 | 6/2004 | Narita et al. |
| 2005/0202084 A1 | 9/2005 | Adusumilli et al. |

(Continued)

FOREIGN PATENT DOCUMENTS

| | | |
|---|---|---|
| BE | 1016566 A4 | 2/2007 |
| BE | 1016895 A6 | 9/2007 |

(Continued)

OTHER PUBLICATIONS

Bolhuis, G.K. et al., DC Calcium lactate, a new filler-binder for direct compaction of tablets, International Journal of Pharmaceuticals, 221:77-86 (2001).
Bruynseels, J. et al., Fluidized-bed process fully established and still developing, Granulation Technology, 183:22-26 (1990).
CPhI Celebrates ten years of growth in Frankfurt, Manufacturing Chemist, (1999).
European Pharmacopoeia 7.0, Dissolution test for solid dosage forms, 2.9.3:20903 (2010).
European Pharmacopoeia 7.0, Resistance to Crushing of Tablets, 2.9.8:20908 (2008).
European Pharmacopoeia 7.0, Uniformity of Content of Single-Dose Preparations, 2.9.7:20906 (2008).
European Pharmacopoeia 7.1, Disintegration of tablets and capsules, 2.9.1:20901 (2011).

(Continued)

Primary Examiner — Patricia Duffy
Assistant Examiner — Garen Gotfredson
(74) Attorney, Agent, or Firm — Choate, Hall & Stewart LLP; Charles E. Lyon

(57) ABSTRACT

Calcium-containing compounds have been at least partly film-coated and/or granulated with a water-soluble substance and a water-soluble polymeric substance and use of such coated compounds in pharmaceutical compositions. The at least partly film-coated and/or granulated calcium-containing compounds have proved suitable for the preparation of tablets having a very high load of elemental calcium and a conveniently small size. A drug load of about 96% or more is obtained in tablets of the invention that have sufficient mechanical and organoleptic properties.

17 Claims, 14 Drawing Sheets

(56) References Cited

U.S. PATENT DOCUMENTS

| | | |
|---|---|---|
| 2005/0244493 A1 | 11/2005 | Withiam et al. |
| 2006/0068005 A1 | 3/2006 | Ross et al. |
| 2006/0159760 A1 | 7/2006 | Yoneyama et al. |
| 2007/0264329 A1 | 11/2007 | Stotler et al. |
| 2009/0004360 A1 | 1/2009 | Bingley et al. |
| 2009/0022792 A1 | 1/2009 | Dittmar et al. |
| 2009/0041860 A1 | 2/2009 | Acebron Fernandez et al. |
| 2009/0142401 A1 | 6/2009 | Appel et al. |
| 2009/0220477 A1 | 9/2009 | Brown |
| 2010/0009948 A1 | 1/2010 | Nelson et al. |
| 2010/0068347 A1 | 3/2010 | Policker |
| 2010/0173859 A1 | 7/2010 | Kolter et al. |
| 2010/0178306 A1 | 7/2010 | Kolter et al. |
| 2010/0178349 A1 | 7/2010 | Kolter et al. |
| 2010/0184785 A1 | 7/2010 | Kolter et al. |

FOREIGN PATENT DOCUMENTS

| | | |
|---|---|---|
| EP | 0647591 A1 | 4/1995 |
| EP | 0872240 A1 | 10/1998 |
| EP | 0914818 A1 | 5/1999 |
| EP | 0988797 A1 | 3/2000 |
| EP | 0999843 A1 | 5/2000 |
| EP | 1126017 A1 | 8/2001 |
| EP | 1369131 A1 | 12/2003 |
| FR | 2081364 A1 | 12/1971 |
| FR | 2717387 A1 | 9/1995 |
| JP | 58008020 | 1/1983 |
| JP | 5306229 | 11/1993 |
| JP | 2001/316249 A | 11/2001 |
| JP | 2002087965 A | 3/2002 |
| JP | 3825269 B2 | 9/2006 |
| WO | WO-92/10168 A1 | 6/1992 |
| WO | WO-95/08273 A1 | 3/1995 |
| WO | WO-96/09036 A1 | 3/1996 |
| WO | WO-97/41835 A1 | 11/1997 |
| WO | WO-98/52541 A1 | 11/1998 |
| WO | WO-99/06051 A1 | 2/1999 |
| WO | WO-99/65473 A1 | 12/1999 |
| WO | WO-0028973 A1 | 5/2000 |
| WO | WO-00/76650 A1 | 12/2000 |
| WO | WO-01/51026 A2 | 7/2001 |
| WO | WO-0176610 A1 | 10/2001 |
| WO | WO-0183374 A2 | 11/2001 |
| WO | WO-2004/080439 A1 | 9/2004 |
| WO | WO-2005/034922 A1 | 4/2005 |
| WO | WO-2005/115342 A1 | 12/2005 |
| WO | WO-2006/047493 A2 | 5/2006 |
| WO | WO-2009/118465 A1 | 10/2009 |
| WO | WO-2009/135947 A2 | 11/2009 |
| WO | WO-2009/135948 A2 | 11/2009 |
| WO | WO-2009/135950 A2 | 11/2009 |

OTHER PUBLICATIONS

Excipient Systems, (2000) http://www.merck.de/english/services/specialchemie/s_chn/pharma/exhipients.htm.

Klobes, P. et al., Porosity and specific surface area measurements for solid materials, National Institute of Standards and Technology, 960(17):1-79 (2006).

Merck Formaxx Products, Marketing Information. (2004).

Oneda, F., The effect of formulation variables on the dissolution and physical properties of spray-dried microspheres containing organic salts, Power Technology, 130:377-384 (2003).

Rumpler, K. and Jacob M., Continuous Agglomeration and Granulation by Fluidization, Food Marketing & Technology, 1-33 (1999).

* cited by examiner

Figure 1A
Figure 1B
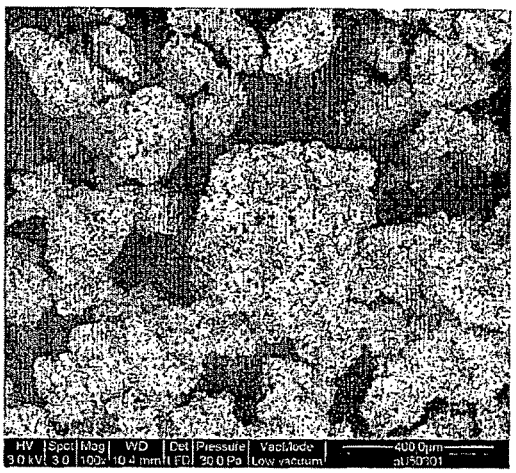
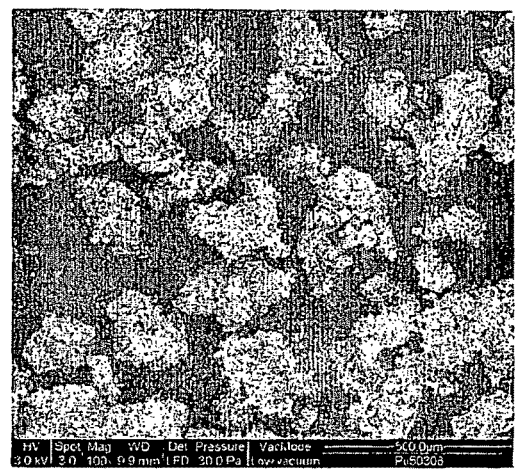
Fig. 1

FILM-COATED AND/OR GRANULATED CALCIUM-CONTAINING COMPOUNDS AND USE THEROF IN PHARMACEUTICAL COMPOSITIONS

CROSS-REFERENCE TO RELATED APPLICATIONS

This application is a Continuation of U.S. National State application Ser. No. 12/085,799, filed May 29, 2008, which claims benefit of International Patent Application No.: PCT/DK2006/000696, filed Dec. 7, 2006, which claims the benefit of U.S. Provisional Application No.: 60/850,130, filed Oct. 6, 2006, and Danish Application Nos. PA 2005 01736, filed Dec. 7, 2005 and PA 2006 01203, filed Sep. 15, 2006, the entirety of each of which is hereby incorporated by reference.

FIELD OF THE INVENTION

The present invention relates to calcium-containing compounds that have been at least partly film-coated and/or granulated with a water-soluble substance and a polymeric substance and use of such coated compounds in pharmaceutical compositions. The at least partly film-coated and/or granulated calcium-containing compounds have proved suitable for the preparation of tablets having a very high load of elemental calcium and a conveniently small size.

BACKGROUND

The present administration of calcium as supplements or medicinal specialties to be taken orally are frequently characterised by a number of disadvantages or inferior technical properties in addition to an unfavourable consumer acceptance.

Calcium is most frequently administered as calcium carbonate as this salt contains a high load of calcium. Normally 500 mg $Ca^{2+}$ equivalent to 1250 mg of calcium carbonate is administered in one dosage. Incorporating 1250 mg of calcium carbonate into a tablet to be swallowed does not represent a good administration form, as the tablet is bulky and not easy to swallow.

An increasingly used dosage form containing calcium carbonate is a chewable tablet formulation as this dosage form presents a more palatable choice for the patient. A further improvement is the tablet melt formulation, which disperses quickly in the mouth without the aid of chewing.

However the chewable tablets and tablet melt formulations have for a number of reasons got inferior technical properties and problems related to an unfavorable consumer acceptance.

Due to a desired high content of calcium carbonate it is often necessary to incorporate a considerable amount of excipients in order to achieve a satisfactory agglomeration to produce a granulate and subsequent a satisfactory compression to form tablets. Another reason for incorporating a fairly high proportion of excipients like soluble filer materials is also carried out in order to achieve a palatable dosage form which disperses quickly in the mouth and which does not stick to the teeth. This give rise to rather large tablets, which the patient or consumer will find difficult to take.

Another disadvantage with the present chewable tablets is that they very often contain soluble filler materials, which are quite hygroscopic. The tablets thus represent a stability problem when stored in humid conditions. This problem requires the need for unnecessary packaging in order to protect the tablets against moisture, which adds to the cost of the product.

Furthermore there is a need to produce a dosage form, which gives the patient a choice with respect to the administration of the tablet.

Elderly and young people quite often prefer dosage forms that are easily dispersed in water, thereby becoming drinkable. There is thus a need for a "multi-function" dosage form, which can be chewed, dispersed in water or which just melts in the mouth.

Them is also a need for a rational and industrial method of manufacture for the production of a small and compact dosage form of calcium with multi-function properties, which does not require the use of costly excipients or the use of costly packaging materials.

Particulate matter or a granular material may be produced by a variety of production processes in pharmaceutical manufacture including high speed mixing, dry granulation or compaction, extrusion, spray drying and fluid bed processing. The most common method of granulation in pharmaceutical manufacture is by high speed mixing or high shear mixing and subsequent drying of the moist granulate in a fluid bed. This method produces a dense granulate which is appropriate for making small tablets with a high density. Fluid bed granulation is much less used as this is a more complicated process and more costly with respect to investment, process validation and running cost. The fluid bed granulation process produces a less dense granulate, which is undesirable when ordinary tablets to be swallowed are to be manufactured.

The successful formulation of calcium chewable products demands very specialized raw materials and most important a very delicate production process. The importance of combining critical characteristics of the raw materials together with a carefully selected production process has been shown for calcium chewable tablets in European Patent Application published under No. 1128815 of Nycomed Pharma AS.

This document describes a process by which the undesirably high bulk of a chewable tablet containing calcium carbonate is reduced. The reduced tablet size has been accomplished by careful selection of the physical properties of the calcium carbonate source and a fluid bed granulation and drying process. The optimal windows for the mean particle size and specific surface area were found to be 3 to 40 µm and 0.1 to 1.2 $m^2/g$, respectively, for the preferred qualities of calcium carbonate. The choice of particle size range was especially important in order to achieve a satisfactory chewability and dispersion in the mouth where as the specific surface area was important in order to accomplish an efficient or short processing time during the granulation and drying phase in a fluid bed. The fluid bed granulation step has resulted in a very homogenous distribution of the binder, which in turn results in a rapid dispersion of the tablet when chewed but also very good consolidation properties during the tabletting step. This last property is very important for the productivity of high speed tabletting machines to ensure maximum output and a minimum demand for cleaning and maintenance of tablet tooling.

However, the use of fluid bed granulation and drying raise some problems that remain unsolved. These problems are both related to the flexibility of the composition of the fluid bed granulate and to processing problems during execution of a batch recipe.

The formulation and processing problems are laid down in the below section:

Trying to make a more compact calcium chewable formulation by reducing the amount of excipients has proved to be difficult due to unsatisfactory agglomeration resulting in a granulate which contained too much fine material. Likewise the subsequent tablet compression has been found to be difficult due to insufficient tableting properties resulting in a non-cohesive tablet with an unsatisfactory high percentage for the friability.

Reducing the level of excipients has also reduced the sensory qualities for the chewable tablet formulation resulting in a reduced customer or patient acceptance.

Regular processing problems are the adherence of a powder or granulate to inner parts of fluid bed apparatus, to the spray nozzles and air filters. Another problem has been fine powder particles being lodged beneath the product screen in the lower plenum where the inlet air passes into the fluid bed. In addition to the gradual deposition of powder layers in the expansion chamber this causes a need for regular cleaning.

During the course of a batch recipe of calcium granulate there have been problems in ensuring a satisfactory fluidization during the end of the granulation step and the beginning of the drying step. Especially during the summer season where the dehumidifying capacity is at its limits there have been problems with insufficient drying and lump formation in the product container. This causes a significant problem of granulate batches, which are not according to specification with respect to the moisture content which is too high.

U.S. Pat. No. 5,939,091: "Method for making fast-melt tablets" by Warner Lambert Company discloses compositions and processes in order to produce fast disintegrating and fast melt tablets containing calcium carbonate.

The patent specifies the use of low density alkali metals with density in the range of 0.3 g/ml to about 0.55 g/ml as these qualities after spray drying or compaction can be compressed into tablets which has a low density and which exhibit quick disintegration in the buccal cavity and a smooth mouth feel. Tablets produced with calcium carbonate based on a denser quality of 0.85 g/ml are described not to result in an acceptable mouth-feel.

However, U.S. Pat. No. 5,939,091 does not describe compositions, which give a fast disintegration at high loadings of calcium carbonate, and, accordingly, does not produce solutions with respect to producing small and dense tablets with rapid disintegration and good sensory properties.

WO 20041047810 A1: "Mannose-based fast dissolving tablets" by Purdue Research Foundation gives an overview over the present technologies and patents for making fast-dissolving, fast-disintegrating or fast-melting tablets. It lists the following table for technologies used in the preparation of fast-dissolving tablets:

|   |   | Advantages | Disadvantages |
|---|---|---|---|
| 1. | Freeze drying | Dissolve within seconds | Highly fragile, expensive |
| 2. | Moulding | Low pressure for making tablets | Poor mechanical strength |
| 3. | Sublimation | No pressure for making tablets | Use of volatile materials |
| 4. | Direct compression | High mechanical strength, low cost | Slow disintegration |

WO 20041047810 A1 discloses a laborious method for producing fast-disintegration tablets with mannose involving first compressing a mannose and drug powder mixture to yield a tablet with very low mechanical strength and secondly to expose this fragile tablet to water vapour or high humidity to establish liquid bridges and where the tablets were subsequently dried to yield tablets with an increased mechanical strength of 40 Newton.

U.S. Pat. No. 6,149,941: "Taste of active pharmaceutical ingredients" by Merck Patent Gesellschaft discloses a process for improving the taste of sold formulations containing one or more active ingredients. The process involves co-spray drying the active together with at least one polyol where both the active and the polyol are dissolved or dispersed in the aqueous phase before commencing the spray drying in either a spray drying equipment or in a fluid bed apparatus.

The patent further discloses that the tabletting behavior of polyols like mannitol, lactitol, isomaltol and xylitol is poor resulting in low tablet hardness, scale-off and severe friability of the tablets. Sorbitol on the other hand was found to give tablets with very good tablet hardness and tablets with particular smooth surfaces. The employment of sorbitol in the compositions from the examples in the patent was in the range of 10 to 33% which gave tablets with improved sensory properties with respect to taste and chewability.

Thus, prior art suggests that dense tablets containing calcium carbonate do not yield tablets with a quick disintegration in the buccal cavity end with an acceptable mouth feel. The prior at also indicates that when formulating chewable tablets it is important to choose a polyol like sorbitol with good mouldable properties.

Furthermore it can be stated that technologies and processes producing tablets with fast disintegration or fast melt properties very often are laborious and costly where conventional pharmaceutical processing equipment cannot be used. Fast melt formulations very often also exhibit unfavorable characteristics like having to use a high percentage of excipients, being hygroscopic and being very friable and unstable to moisture.

There is thus a need to produce an improved solid and oral dosage form containing a calcium compound with the following properties:
High loading of calcium in order to produce a small and dense tablet
Fast disintegration or fast melt properties
Good sensory properties
Multi-function properties where the tablet can be chewed, melted in the mouth or dissolved in a glass of water to be taken as a liquid dosage form
Good tablet compression characteristics to yield tablets with a high degree of mechanical strength
A robust tablet formulation which can withstand normal moisture challenges from the environment
The employment of standard pharmaceutical equipment and a short processing time.

SUMMARY OF THE INVENTION

The present invention provides such improved compositions. The present invention is based on the finding that— when a water-soluble film comprising a water-soluble substance and a polymeric substance at least partly is applied on the calcium-containing compound—then only small amounts of excipients are required in order to manufacture e.g. tablets having suitable properties as those mentioned above. Moreover, it is possible to obtain tablets of relatively small size and containing 96% w/w or more of the calcium-containing compound; notably a content of the calcium-containing compound of about 97% w/w can be made.

Thus, calcium chewable tablet formulations with excellent sensory properties have been produced with an amount of excipients, which have been reduced to a level of approximately 2-16.6% of the tablet weight. The chewable and melt formulations containing 500 mg $Ca^{2+}$ equivalent to 1250 mg of calcium carbonate have a tablet weight of 1290 to 1500 mg and a tablet diameter of 13 to 15 mm.

This has been achieved due to a surprising synergistic effect which has taken place leading to a fast agglomeration with a reduced amount of fine material and—in a subsequent tabletting step—resulting in tablets with very good cohesive properties produced at low tabletting pressures. The synergistic effect is achieved by applying a composition containing a water-soluble substance and a polymeric substance on the calcium-containing compound in order to obtain a water-soluble film at least partly on the calcium-containing compound. Without being bound to theories, plastic properties may also be important in a subsequent tabletting step in order to ensure good cohesive properties. Moreover, the solid components included in the composition must be water-soluble, i.e. the polymeric substance must also be water-soluble.

Accordingly, in a separate aspect, the invention relates to an at least partly film-coated calcium-containing compound, wherein the calcium-containing compound is in the form of particles and/or crystals that at least partly are provided with a soluble film coating having binding properties.

The present invention also relates to a method for the preparation of an at least partly film-coated calcium-containing compound, the method comprising applying a coating composition comprising one or more water-soluble substances and one or more polymeric substances on a calcium-containing compound.

Furthermore, the present invention relates to a number of compositions, notably tablet composition that has one or more, preferably all the above listed characteristics.

Accordingly, in a further aspect, the present invention relates to a composition comprising an at least partly film-coated calcium-containing compound as described herein and one or more pharmaceutically acceptable excipients. Furthermore, the invention relates to a method for the preparation of such a composition, the method comprising mixing one or more pharmaceutically acceptable excipients with the at least partly film-coated calcium-containing compound.

In a still further aspect, the invention relates to a method for improving the taste of a calcium-containing compound, the method comprising applying a film coating containing one or more water-soluble substances and a polymeric substance on a calcium-containing compound in the form of particles and/or crystals to obtain an at least partly film-coated calcium-containing compound as defined herein.

In some cases—depending on the manufacturing method—it may be difficult to judge the extent of coating on the calcium-containing compound. However, the coating process is also a granulation process and, accordingly, in another aspect, the invention related to a granulated calcium-containing compound that has been granulated with a granulating composition comprising a water-soluble substance and a polymeric substance. Coating refers to a complete or partly complete covering of the surfaces of the calcium carbonate crystals which takes place at the start of the coating and agglomeration process in a fluid bed spray granulator. This complete or partly complete coverage of the combined polymeric binder and soluble filler causes a rapid agglomeration or granulation to take place. The subsequent application of the granulation and coating liquid will then mainly cause a further coating to take place where the surfaces of the granules will receive a more extensive coating. However there will also at the same time take place a further binding of dust and fine particles to the surfaces of the initial granules. Thus the method of manufacture is a combined agglomeration and coating process where the primary particles or crystals receive a complete or partial coating, the coated particles are then agglomerated and the granules are then further coated. This is evident by the very rapid dispersion of the primary particles when a calcium melt tablet according to the invention is exposed to an aqueous environment.

All details and particulars described relating to the coating aspect apply mutatis mutandis to the granulate aspect, cf. the appended claims.

In a specific embodiment, the present invention provides a compact calcium chewable composition, which disperses very quickly in the mouth at low excipient levels and with multi-function properties comprising; a chewable tablet; a tablet to be swallowed; a met tablet formulation and an aqueous dispersible formulation. In a specific embodiment, the composition comprises the following components:
(a) a calcium-containing compound (CC) having a surface area of 0.1 to 1.5 $m^2/g$
(b) a combination of a water-soluble substance and a polymeric substance with binding properties;
the composition is prepared by
(c) dissolving the combined water-soluble substance and the polymeric substance to produce a granulation and coating liquid.
(d) applying the granulation and coating liquid in a fluid bed apparatus onto the fluidized bed of the calcium-containing compound, and,
(e) optionally mixing the granulate obtained with other excipients and compressing it into chewable or melt tablets.

The fluid bed granulation step has resulted in the formation of granules or agglomerates of individually coated particles or crystals of the calcium-containing compound. It has also been observed that the coating layers may include or fixate the fine material fraction of the calcium-containing compound into the film surrounding the individual particles or crystals.

In a preferred embodiment, the resultant chewable tablets are characterized by the following properties:
  A dense tablet with apparent tablet densities in the range of from 1.4 to 1.9 $g/cm^3$.
  A multi-function fast melt tablet which can be chewed, dispersed quickly within 60 sec in the mouth without chewing, dispersed within 180 sec in a glass of tap water or swallowed. In a specific embodiment as illustrated in the Examples herein using the fluid-bed technology, a melt tablet can be produced that disperses quickly within 30 sec in the mouth without chewing, and which disperses within 60 sec in a glass of tap water
  The tablets contain a high load of active ingredients up to 96% or 97% of the tablet weight.
  The tablets are produced at low tabletting pressures of 6 to 46 kN. In a specific embodiment, the tabletting pressures may be as low as from 6 to 20-25 kN or even lower from 6 to 16 kN. The pressure applied also depends on the tablet machine employed and whether it is a production or pilot scale.

The tablets are robust with a friability of less than 2% and can withstand ordinary packaging machines.

The tablet composition does not require high cost special excipients

The tablets can be produced on existing and ordinary production and packaging equipment.

The tablets are non-hygroscopic.

The tablets are contemplated not to require special packaging protection.

The process time is short and the tablets can be produced at a low cost.

The new formulation principle of combining a water-soluble substance and a polymeric substance with binding properties has also resulted in processing advantages during the fluid bed process including a shorter processing time, less generation of fines, a reduction of adhesion of fine powder to the inside of the product container and expansion chamber and probably a reduction of the accumulation of fine powder in the lower plenum due to a faster agglomeration speed.

It has also surprisingly been found that the mean particle size of the at least party film-coated calcium-containing compound can be effectively varied over a wide particle size range by carefully controlling the content of the polymeric substance and the amount of granulation liquid employed during the granulation step.

Furthermore it has surprisingly been found out that the new formulation principle is much less sensitive to processing difficulties and variation in moisture content and particle size/distribution of the granulate when different sources of calcium are employed with different physical characteristics like specific surface area, particle size/distribution and particle shape.

BRIEF DESCRIPTION OF THE DRAWINGS

FIG. 1A depicts at least partly film coated and agglomerated calcium carbonate crystals according to example 1.

FIG. 1B depicts a granulate according to European application EP-A-1128815 of Nycomed
  Pharma consisting of calcium carbonate (74.5%), sorbitol (23.3%) and copovidone (2.2%) where a 28% solution of copovidone has been employed during the granulation step in a pilot scale Glatt GPCG 3 fluid bed.

DETAILED DESCRIPTION OF THE INVENTION

Figure 2:
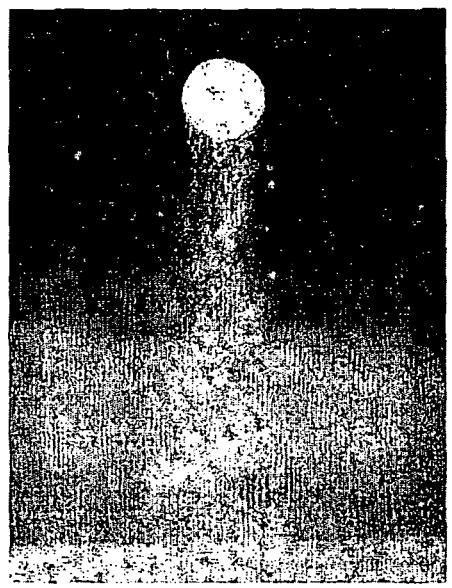
FIG. 2 illustrates the "Hanging Tablet" method.

As mentioned above, there is a need for improving dosage forms containing calcium-containing compounds in order to make these smaller, more palatable and also to introduce flexibility with respect to the intake of the dosage form. There is also a need to establish a production method which is rational and cost saving and which utilize standard pharmaceutical processing equipment.

The invention is based on the finding that it is possible at least partly to coat a calcium-containing compound with a combination of a water-soluble substance and a polymeric substance. Such a coating seems to be very advantageous as it at least partly encapsulates the calcium-containing compound in such a way that the amount of the normally employed fillers and taste-improving agents used in the manufacturing of the end product can be reduced without leading to a product that has poorer sensoric properties.

At Least Partly Film-Coated Containing Compounds or Calcium-Containing Combinations or Compositions Accordingly, in one aspect the invention relates to an at least partly film-coated calcium-containing compound, wherein the calcium-containing compound is in the form of particles and/or crystals that are at least partly provided with a water-soluble film coating.

It is believed that it is not necessary to coat the whole available surface of the calcium-containing compound in order to obtain the desired effect, i.e. to obtain compositions that have acceptable sensoric properties when tested by a professional taste panel of at least 6 persons and/or to obtain tablets that have a very high load of calcium and a convenient small size.

In order to obtain the desired effect it is envisaged that at least 50% such as, e.g., at least about 60%, at least about 70%, at least about 75%, at least about 80%, at least about 90%, at least about 95%, at least about 99% or 100% of the surface area of the calcium-containing compound is covered with the film coating.

The film covering the calcium-containing compound may be a continuous film, i.e. a film that substantially covers the outer surface of the calcium-containing compound.

In order to judge to which extent the surface of the calcium-containing compound is coated with a film-coat it is possible to study SEM pictures of the coated compound. Other methods may also be employed such as ESEM (Environmental Scanning Electron Microscopy), X-ray Photo Electron Spectroscopy, TOF-SIMS (Time-of-light secondary ion mass spectrometry) etc.

As mentioned above, it is important that the extent of coating is sufficient for the specific purpose. Accordingly, the following test may be used in order to evaluate whether the coating is applied to a sufficient extent.

Prepare a tablet by
i) mixing the at least partly film-coated calcium-containing compound with a lubricant such as, e.g., magnesium stearate to obtain a mixture wherein the concentration of the at least partly film-coated calcium-containing compound is 99.5% w/w, and
ii) compressing the thus obtained mixture into tablets,
subject the obtained tablet to the "Hanging Tablet" method described herein, and the observed slip time should be at the most 3 min such as at the most 2 min, at the most 1 min, at the most 45 sec or at the most 30 sec.

The above-mentioned test is especially relevant when the end product is a melt tablet or a chewing tablet:

Furthermore, the above-mentioned test is especially suitable for use when the film-coating has been performed in a fluid-bed apparatus.

Alternatively, prepare a tablet by i) mixing the at least partly film-coated calcium-containing compound with a sugar alcohol such as, e.g., xylitol and a lubricant such as, e.g., magnesium stearate to obtain a mixture wherein the concentration of the at least partly film-coated calcium-containing compound is at least 80% w/w, the concentration of the sugar alcohol is at the most 19.5% w/w, and the concentration of the lubricant is at the most 2%, and ii) compressing the thus obtained mixture into tablets, subject the obtained tablet to a sensoric test by a professional test panel, which must find the sensoric properties of the tablet acceptable.

However, the coating process is in fact a combination of a coating and an agglomeration process, i.e. the calcium-containing compound is coated and agglomerated with a highly soluble film with good binding and/or tablet consolidation properties. Thus, pharmaceutical processes, which can apply coating and agglomeration of individually crystals or particles e.g. with a small size in the range of 5 to 40 µm, can be used in the present context. Accordingly, it is envisaged that other granulation or coating methods are equally suitable (cf. the Examples herein) such as, e.g. other wet or melt granulation methods or other coating methods such as spray coating or melt coating. Agglomeration and coating equipment include batch and continuous fluid beds with top, bottom or tangential spray like systems from Glatt, Aeromatic and Heinen, horizontal and vertical high intensive mixers like Fielder or Diosna, continuous mixers like Schugi from Hosokawa, extruders like twin screw extruders or spray drying equipment in combination with internal or secondary fluid bed units from e.g. Niro or Anhydro.

Agglomeration, also termed granulation, is a process where particles are brought together into larger aggregates, so called agglomerates or granules, where the original particles are still distinguishable. In wet agglomeration, this process is facilitated by a granulation liquid. The liquid binds the particles by a combination of capillary and viscous forces in the wet state. More permanent bonds are formed during subsequent drying. The aim of agglomeration is to improve powder flow and handing, decrease dustiness, fixation of mixture and thereby prevent segregation of the API (active ingredient).

The strength of the agglomerates depend on the bonds formed during drying. The strength of the bonds can be improved by adding a polymer to the granulation liquid, which also can lead to improved tableting properties. However, the adding of polymer to the granulation fluid can result in prolonged disintegration times, curing of tablets, decrease in melt properties etc.

Wet agglomeration can be carried out with e.g. High shear mixer, Schugi Flex-O-Mix agglomerator and fluid bed among other equipments.

Fluid Bed: Fluid bed granulation and drying takes place in a fluid bed spray granulator consisting of a product container and an expansion chamber for fluidization of the powder mixture to be granulated. The powder mixture is resting on a product screen at the bottom of the product container and restricted from escaping the expansion chamber by an exhaust filler on the outlet side of the fluid bed spray granulator. The airflow necessary for fluidization of the powders is generated by a suction fan mounted in the top portion of the unit. The air used for fluidization is heated to the desired temperature by an air heater positioned in the air inlet portion of the equipment. The powder mixture is fluidized by a sufficient air volume and the granulation liquid is atomized as a fine spray through a spray head consisting of a multiple of binary nozzles. The spray head may add the atomised spray of granulation liquid counter-current to the pulsating particles denoted "top spray" or co-current to the pulsating bed denoted "bottom spray". The wetted particles undergo agglomeration or granulation through particle—particle contacts. After appropriate agglomeration is achieved, the spray operation is discontinued and the material is dried and discharged from the unit. By adjusting the critical formulation characteristics and process parameters for the fluid bed process it is possible to agglomerate, instantize or coat individual particles in a powdery mixture.

High Shear mixer: In this type of equipment, the particles are set into movement by an impeller rotating at a high speed. It contains also a chopper which breaks large aggregates. The binder liquid is added by pouring, pumping or spraying from the top. Wet agglomeration in a high-shear mixer involves typically five to six phases: First the materials are dry mixed, where after liquid is added during mixing. Then the moist mass is wet massed. Thereafter the granules are (wet sieved), dried and sieved again.

Schugi: A typical Schugi Flex-O-Mix agglomerator procedure involves the following general steps. The dry feed product is by gravity fed to the top of a cylindrical chamber which contains a rotating inner shaft (about 1000-4400 RPM) with attached knives. At the point where the dry feed product enters the chamber, a granulation liquid is introduced to the powder by atomisation. The dry feed powder and granulation liquid are violently and intimately mixed causing particle collisions and subsequent particle growth. The sides of the Schugi cylindrical chamber are made of a flexible material, so that during operation a device can periodically squeeze the chamber causing powder build up to dislodge. The particles are then immediately fed to a dryer to remove excess moisture.

The film comprises a water-soluble substance and a polymeric substance, notably a polymeric water-soluble substance. Normally, the polymeric substance has binding properties, which is useful as the coating process also enables formation of agglomerates to provide a granulate. The water-solubility of the polymeric substances is about 10 mg/ml or more such as, e.g., about 25 mg/ml or more, about 50 mg/ml or more, about 75 mg/ml or more, about 100 mg/ml or more, about 150 mg/ml or more, about 200 mg/ml or more, about 250 mg/ml or more, or about 300 mg/ml or more.

The water-soluble substance in the coating is important as it confers water-solubility to the coat and contributes to the fast disintegration and/or dissolution observed for tablets based on the at least party film-coated calcium-containing compound according to the invention. The water-solubility of the one or more water-soluble substances is about 10 mg/ml or more such as, e.g., about 25 mg/ml or more, about 50 mg/ml or more, about 75 mg/ml or more or about 100 mg/ml or more.

The table below gives water-solubilities for water-soluble substances (also denoted water-soluble filler materials) for use according to the invention.

| Water-soluble substances for use in coating compositions | Solubility in water at 20° C. |
|---|---|
| Xylitol | 1 in 1.6 |
| Sorbitol | 1 in 0.5 |

-continued

| Water-soluble substances for use in coating compositions | Solubility in water at 20° C. |
|---|---|
| Mannitol | 1 in 5.5 |
| Maltitol | Freely soluble |
| Lactitol | 1 in 1.75 |
| Erythritol | 1 in 1.2 |
| Isomalt | 1 in 4 |
| Isomaltulose | 1 in 2.8 |
| Maltodextrins | Freely soluble |
| Sucrose | 1 in 0.5 |
| Oligofructose | 1 in 1.3 |
| Cyclodextrins | |
| α-cyclodextrin | 1 in 7 |
| β-cyclodextrin | 1 in 50 |
| γ-cyclodextrin | 1 in 4.4. |

Normally, the soluble filer material should have a solubility larger than 1 g/100 ml.

Examples of suitable water-soluble substances for use according to the invention are polyols and carbohydrates, and mixtures thereof.

Other examples of suitable water-soluble substances are organic acids, pharmaceutically acceptable salts of organic acids including alkali metal and alkaline earth metal salts (e.g. carbonates, citrates, acetates, fumarates, etc exemplified in the examples with citric acid and sodium ascorbate), amino adds (e.g. glycine), inorganic salts including sodium chloride etc.

Typically, the polyol is a sugar alcohol. In specific embodiments, the sugar alcohol is selected from the group consisting of xylitol, sorbitol, mannitol, maltitol, lactitol, erythritol, inositol, isomalt, isomaltulose and mixtures thereof.

The water-soluble substance may also be carbohydrate selected from the group consisting of mono-, disaccharides, oligosaccharides, polysaccharides, and mixtures thereof.

Examples of suitable monosaccharides for use according to the invention are glucose, mannose, fructose, galactose, and mixtures thereof. Examples of suitable disaccharides for use according to the invention are lactose, maltose, sucrose, trehalose, tagatose, and mixtures thereof; and examples of suitable oligosaccharides and polysaccharides for use according to the invention are dextrose, oligofructose, cyclodextrins, maltodextrins, and mixtures thereof.

Normally, the water-soluble substance is present in the at least partly film-coated calcium-containing compound in a concentration from 0.1% w/w to about 50% w/w such as, e.g., 0.5% w/w to about 50% w/w 0.75% w/w to about 50% w/w, from about 1% w/w to about 40% w/w, from about 1.5% w/w to about 30% w/w, or from about 2% to about 20% w/w.

In specific embodiments, the concentration of the water-soluble substance in the at least partly film-coated calcium-containing compound may be in a lower concentration range such as from about 0.1% w/w to about 10% w/w such as, e.g., from about 0.5% w/w to about 10% w/w from about 1% w/w to about 10% w/w, or from about 2% w/w to about 5% w/w.

As mentioned above, the polymeric substance used in the coating of the calcium-containing compound must have good binding and/or tablet consolidation properties. Such properties are important in the further manufacturing of the obtained at least partly film-coated calcium-containing compound, especially in the manufacturing of tablets. The good binding and/or tablet consolidation properties may also be plastic properties. Such properties makes it possible to substantially avoid breakage or otherwise destruction of the film-coat, thus, the properties obtained by the film coating are also present in the end product.

Moreover, it is advantageous if the polymeric substance has binding properties and thereby enables agglomeration of the calcium-containing compound (optionally together with one or more pharmaceutically acceptable excipients). Examples of such polymeric substances with binding properties are found among pharmaceutically acceptable binders. Accordingly, in a specific embodiment, the polymeric substance is a pharmaceutically acceptable binder.

The polymeric substances may be selected from different types of povidones, copovidones, cellulose type polymers, inulin and oligosaccharides, high molecular weight polysaccharides and starches. Specific examples can be found under the heading "Pharmaceutically acceptable excipients" and in the examples herein.

Examples of pharmaceutically acceptable binders that are suitable for use according to the present invention are povidones including K-90, K-30, K-25, K-17 and K-12; copovidone; polyethylene glycol-polyvinylalcohol (e.g. Kollicoat IR), agar; gelatin; gummi arabicum; alginates including sodium alginate and polyetylene glycol alginate; starches or modified starches including potato starch, maize starch, rice starch, pre-gelatinised starch; carbohydrates including inulin, polydextrose, dextrin, malodextrins; cellulose and cellulose derivatives including sodium carboxymethylcellulose, hydroxypropylcellulose, hydroxypropylmethylcellulose (HPMC), microcrystalline cellulose, cellulose derivatives such as low-substituted hydroxypropylcellulose, and mixtures thereof.

The concentration of the polymeric substance used in the at least partly film-coated calcium-containing compound may vary dependent on the particular polymeric substance employed. In general, the concentration is in a range from about 0.09% to about 10% w/w such as from about 0.2% to about 10% w/w, from about 0.5 to about 5% w/w.

The calcium-containing compound is selected from the group consisting of calcium carbonate, calcium citrate, calcium lactate, calcium phosphate including tricalcium phosphate, calcium gluconate, bisglycino calcium, calcium citrate maleate, hydroxyapatite including solvates thereof, and mixtures thereof.

In specific embodiments, the calcium-containing compound is calcium carbonate or a calcium phosphate (including dicalcium phosphate and tricalcium phosphate), or mixtures thereof. Of particular interest is calcium carbonate.

The specific surface area of the calcium-containing compound employed is of interest especially in those cases where fluid bed granulation is involved in the manufacturing process. Accordingly, in such cases, the specific surface area of the calcium-containing compound such as, e.g., calcium carbonate is from about 0.1 to about 3 $m^2/g$ such as, e.g. from about 0.1 to about 2.75 $m^2/g$, from about 0.1 to about 2.5 $m^2/g$, from about 0.1 to 10 about 2 $m^2/g$, from about 0.1 to about 1.8 $m^2/g$, from about 0.1 to about 1.5 $m^2/g$, from about 0.1 to about 1.6 $m^2/g$, from about 0.1 to about 1.4 $m^2/g$ or from about 0.1 to about 1.3 $m^2/g$.

With respect to calcium carbonate, the specific surface area is normally from about 0.1 to about 1.2 $m^2/g$.

As mentioned herein before, it is generally recognized that the particle size of the calcium-containing compound is of importance for the sensoric properties of the final product. Accordingly, in a specific embodiment, the mean particle size of the calcium-containing compound such as, e.g., calcium carbonate is from about 0.1 µm to about 100 µm such as from about 0.1 μm to about 80 μm, from about 0.5 μm to about 60 μm, from about 1 μm to about 50 μm or from about 2 μm to about 40 μm.

In a further embodiment, the mean particle size of the calcium carbonate is from about 3 to about 40 μm.

The examples herein demonstrate that a particular suitable coating obtained is when the water-soluble substance is xylitol and the polymeric substance is a povidone or copovidone, or mixtures thereof.

Moreover, in a specific embodiment the coating essentially contains the water-soluble substance, notably a sugar alcohol, and the polymeric substance, notably a polyvinylpyrrolidone.

The at least partly film-coated calcium-containing compound may be combined with one or more active substances such as, e.g., a therapeutically active substance and/or a nutrient.

Of particular interest are compositions in which the at least partly film-coated calcium-containing compound is present in combination with a vitamin such as, e.g., vitamin D including vitamin $D_2$ and $D_3$, vitamin B or vitamin K, and derivatives thereof.

In another aspect of the invention a film-coat is applied to a combination of a calcium-containing compound and one or more further substances. The one or more further substances may be another active substance such as those mentioned above, or it may be one or more pharmaceutically acceptable excipients or additives. As seen from the examples herein, a specific embodiment of the invention is an at least partly film-coated composition comprising a calcium-containing compound and one or more polyols such as those mentioned herein before. Additives such as one or more flavoring agents, taste-masking agents, sensory improving agents, acidulants, sweeteners including artificial sweeteners and intense sweeteners may also be present in the composition that at least partly is provided with a film-coating.

In general, the concentration of such further substances present in an at least partly film-coated composition is at the most about 20% w/w such as, e.g., at the most about 15% w/w, at the most about 10% w/w, at the most about 7.5% w/w, at the most about 5% w/w or in a range of from about 0.5 to about 5% w/w. With respect to artificial sweeteners the concentration is normally even lower such a at the most about 1% w/w or at the most about 0.01% w/w.

In other words, normally the calcium-containing compound constitutes at least 80% w/w such as at least 85% or at least about 90% w/w of the total weight of the at least partly film-coated composition.

In a specific embodiment, the at least partly film-coated combination according to the invention further comprises one or more pharmaceutically acceptable excipients.

Besides the possibility that a composition comprising the above-mentioned substances together with the calcium-containing compound at least partly may be provided with a film coating, it is also possible to add such substances to the coating composition. In such cases, the film coating will also contain such substances. To this end, sucralose has been used in some of the Examples herein as an example of an intensive sweetener that has been dissolved in the film-coating composition (which is the same as the granulation liquid) before the coating processing e.g. in fluid bed. Other excipients that may be added to the granulation and coating liquid are colours, flavours, acidulents, surfactants and emulsifiers.

Typically the percentage dry matter in the coating composition (e.g. a solution) has been in the range of 40-70% w/w. In those cases where fluid bed is used, the coating and granulation processing time is typically short in the range of 6-20 min such as in the range of 10-20 min including preheating/mixing, coating/granulation, drying and cooing.

Compositions, Especially Pharmaceutical Compositions, Comprising at Least Partly Film-Coated Calcium-Containing Compounds, Combinations or Compositions As mentioned above, the at least partly firm-coated calcium-containing compounds, combinations or compositions described above are especially suitable in the preparation of pharmaceutical compositions. Accordingly, in a separate aspect, the invention relates to a composition comprising an at least partly film-coated calcium-containing compound and one or more pharmaceutically acceptable excipients.

A composition according to the invention may be used in the manufacture of a pharmaceutical or nutritional composition.

The composition may have any suitable form such as, e.g., being in particulate form such as e.g. powders, granules, granulates, beadlets, pellets etc. or it may be in a dosage form such as, e.g., tablets, capsules, sachets etc. The composition may also be in liquid form or presented in dry form intended to be dispersed in a suitable medium before ingestion.

In a particularly interesting embodiment of the invention, the composition is in the form of a tablet, notably a melt tablet or a chewing tablet.

As mentioned above, the at least partly film-coated calcium-containing compound, combination or composition is particularly suitable to use in the preparation of high-load calcium products. Accordingly, in one embodiment the concentration of the calcium-containing compound is 50% w/w or more such as, e.g., 55% w/w or more, 60% w/w or more, 65% w/w or more, 70% w/w or more, 75% w/w or more, 80% w/w or more or 85% or more in the composition (pharmaceutical composition). Notably, the composition is in the form of a tablet and the concentration of the calcium-containing compound in uncoated form is 80% w/w or more, 85% w/w or more, 90% w/w or more, 95% w/w or more, 96% w/w or more, or 97%% w/w or more.

Tablet Density and Porosity

Tablet density was found to be an important parameter in the development as a high value for the apparent tablet density gave rise to compact and small tablets with a low tablet volume. At the same time it is equally important that the tablet has a sufficient porosity in order to facilitate the dispersion of the tablet in the aqueous phase that being in the mouth or in a glass of water. In the Examples herein, the tablet density and porosity were calculated by measuring the true density of the tablet and the volume of the same tablet by an AccuPyc 1330 instrument and a GeoPyc 1360 instrument respectively, both from Micromeretics.

The focus of the developmental work has also been to make smaller and compact tablets. As seen from the examples herein, this has suitably been achieved. Accordingly, the invention also provides tablets containing the at least partly film-coated calcium-containing compound, combination or composition, wherein the tablet has an apparent density of at the most about 2.2 $g/cm^3$ such as, e.g., at the most about 2.0 $g/cm^3$, at the most about 1.8 $g/cm^3$, or in a range from about 1.4 $g/cm^3$ to about 2.2 $g/cm^3$. In more specific embodiments, the tablet has an apparent density of 1.4 $g/cm^3$ or more such as, e.g. about 1.5 $g/cm^3$ or more or in range of from about 1.4 $g/cm^3$ to about 1.9 $g/cm^3$ or from about 1.5 $g/cm^3$ to about 1.7 $g/cm^3$. It must be emphasized that these density intervals are based on calcium carbonate as the calcium containing compound. Other calcium salts or combinations of calcium salts will create other density intervals based on the differences in the true and apparent densities of these compounds.

The chewable and melt tablet formulations described in some of the Examples have tablet densities in the range of 1.4 to 1.9 g/cm$^3$. Typically a calcium chewable and melt formulation according to the invention will have a tablet density of 1.5-1.7 g/cm$^3$. A tablet according to the invention with this density has at the same time a satisfactory high value for the tablet porosity in the range of 30 to 40% with typical values of 32 to 36%.

The possibility of obtaining small tablets does not affect the possibility of maintaining a suitable porosity, i.e. a porosity that is important when the tablets are melt tablets or chewing tablets. Accordingly, the tablet may have a porosity of from about 10 to about 50% such as, e.g., from about 15 to about 40% or from about 20 to about 40%. In specific embodiments, the tablet has a porosity of from about 30 to about 40%.

Another measure of a small tablet is the tablet volume per 500 mg of elemental calcium contained in a tablet according to the invention. Accordingly, the volume of a tablet according to the invention is normally at the most 1.5 cm$^3$ such as, e.g., at the most about 1.25 cm$^3$, at the most about 1 cm$^3$, at the moat about 0.8 cm$^3$, at the most about 0.7 cm$^3$ or at the most about 0.65 cm$^3$ per 500 mg of elemental calcium contained in the tablet.

Tablet Disintegration and Dispersion

Tablet disintegration and dispersion have been investigated by three different methods in order to characterize this important property.

Firstly a disintegration test according to the European Pharmacopoeia (Ph. Eur.) version 5.02 has been carried out for all of the formulations. Ph. Eur. states that chewable tablets do not have to comply with the test but also defines three other dosage forms which are relevant for the description of the invention: soluble tablets are tablets intended to be dissolved in water before application; dispersible tablets are tablets intended to be dispersed in water before administration and orodispersible tablets which are tablets intended to be placed in the mouth where they disperse before being swallowed. The requirement with respect to the disintegration time for soluble, dispersible and orodispersible tablets according to Ph. Eur. is that these dosage forms should disintegrate within 3 min.

A tablet according to the invention normally has a disintegration time as measured according to Ph. Eur. of at the most about 30 min such as, at the most about 20 min, at the most about 15 min, at the most about 10 min, at the most about 5 min, at the most about 4 min or at the most about 3 min.

In specific embodiments, a tablet according to the invention complies with the Ph. Eur. Typically a calcium melt tablet according to the invention will disintegrate within 60 to 90 seconds.

The inventors have developed another method that especially is suitable to simulate the situation within the mouth. The method is called "Hanging Tablet" method. In this method a hole is drilled in the middle of the tablet and a nylon string is tied to the tablet. The tablet is then dropped into a tank of water and kept suspended in the water at 37° C. by the aid of the string. The visual disintegration/dispersion of the tablet in the aqueous medium is noted together with the time it takes for the tablet to disengage itself from the tied string. The enclosed picture in FIG. 2 best illustrates the method.

The Ph. Eur. disintegration time is a bit more unspecific compared to the "Hanging Tablet" method with respect to measuring the disintegration time in the mouth. There may still be a lump of tablet material resting on the screen in the disintegration apparatus even if the tablet has been fully dispersed. When the tablet has been fully dispersed it means that all the primary calcium carbonate particles have been fully wetted and released from each other.

A tablet, which is suspended from a thread in the "Hanging Tablet" method, will disengage itself from the thread when the tablet has been fully wetted or dispersed with a resultant collapse of the internal structure in the tablet Thus, this method is more alike to what will occur in the mouth if there is a sufficient amount of saliva to be drawn into the matrix and disperse the primary particles of calcium carbonate.

Normally, a tablet according to the invention has a slip time (or dispersion time) as measured by the "Hanging Tablet" method as described herein of at the most about 180 sec, such as at the most about 150 sec, at the most about 100 sec, at the most about 80 sec, at the most about 45 sec or at the most about 30 sec.

In specific embodiment, the dispersion time by the "Hanging tablet" method is typically less than 30 seconds for the compositions according to the invention. Furthermore does the dispersion time correlate well with the actual perceived dispersion time in the mouth as described below.

Dispersion of Tablets Such as, e.g., Melt Tablets in the Mouth

A sensory panel of six selected assessors was used in order to determine the melt dispersion time in the mouth. The average time for the tablet to melt in the mouth and the contents to be swallowed was noted for selected formulations according to the invention. Statistical differences were detected employing ANOVA with 95% confidence level and Tukey's HSD test with a significance level of 5% to discriminate among the means.

Figure 6:
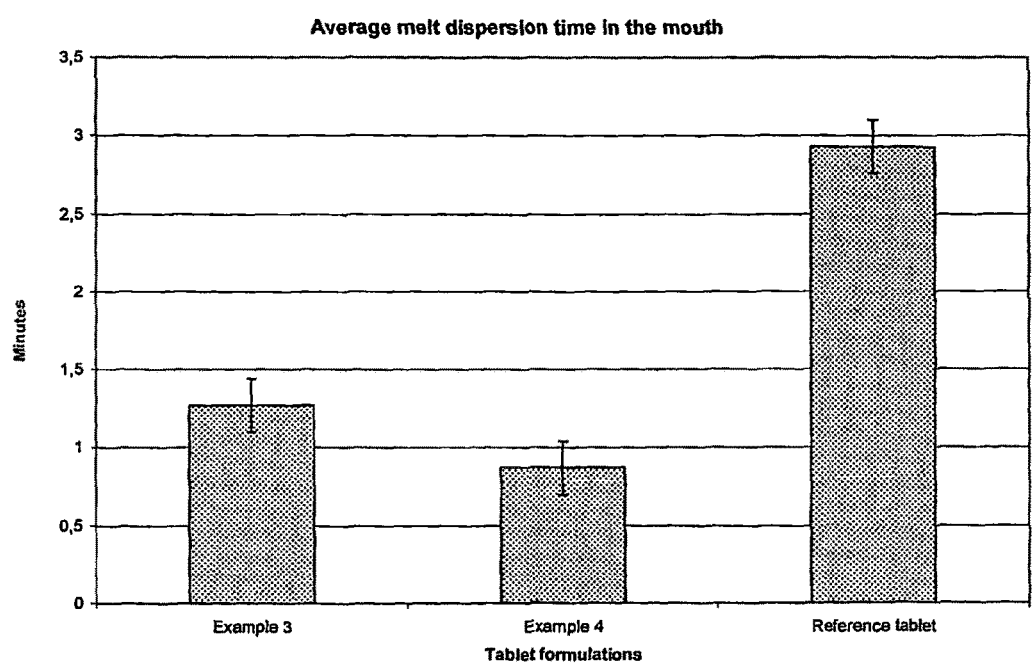
FIG. 6 illustrates melt characteristics for formulations according to the invention.

Two compositions according to the invention were tested against a reference based on a calcium chewable tablet according to European application EP-A-1 128815 of Nycomed Pharma. Both of the formulations according to the invention came out with a significantly shorter melt dispersion time when compared against the reference tablet. The formulation with the best melt characteristics dispersed after 52 seconds. The results have been depicted in FIG. 6.

Dissolution Rate

As it appears from the Examples herein, use of an at least partly film-coated calcium-containing compound, combination or composition according to the invention for the manufacture of tablets can lead to tablets that very rapidly release the calcium-containing compound. Accordingly, at least 60% of the calcium-containing compound is released from the tablet within 30 minutes, at least 70% of the calcium-containing compound is released from the tablet within 30 minutes, at least 80% of the calcium-containing compound is released from the tablet within 30 minutes, at least 60% of the calcium-containing compound is released from the tablet within 20 minutes, at least 70% of the calcium-containing compound is released from the tablet within 20 minutes, at least 80% of the calcium-containing compound is released from the tablet within 20 minutes, at least 60% of the calcium-containing compound is released from the tablet within 10 minutes, at least 70% of the calcium-containing compound is released from the tablet within 10 minutes, at least 80% of the calcium-containing compound is released from the tablet within 10 minutes as measured by an in vitro dissolution test according to Ph. Eur./USP (paddle, 50 rpm dissolution medium: 1000 ml 0.1 M HCl containing 0.04% cetrimide, 37° C.)

In the Examples herein, dissolution analysis was carried according to Ph. EurJUSP with dissolution apparatus 2 (Paddle apparatus) and with a paddle speed of 50 rpm. The dissolution medium was 0.1 M HCl with the addition of the cationic surfactant cetrimide, 0.04%(w/v). The concentration level of 0.04%(w/v) cetrimide in 0.1 N HCl defines the critical micelle concentration. Cetrimide is added in order to reduce the surface tension The dissolution rates for Examples 1 and 2 according to the invention were typically very fast and about 90% was dissolved already after ten minutes. In contrast the dissolution rates for the two reference examples were quite slow and only 17 to 42% w/w was dissolved after 10 min.

Other Ingredients in a Composition Comprising an at Least Partly Film-Coated Calcium-Containing Compound, Combination or Composition According to the Invention As mentioned above other ingredients than the at least partly film-coated calcium-containing compound, combination or composition may be incorporated in a composition of the invention. Thus, one or more active substances such as, e.g., a therapeutically active substance and/or a nutrient may be present including a vitamin such as, e.g., vitamin D including vitamin $D_2$ and $D_3$, vitamin B or vitamin K, and derivatives thereof.

Moreover, one or more pharmaceutically acceptable excipients (suitable examples are described below) or additives may be incorporated. One or more flavoring agents, taste-masking agents, sensory improving agents, acidulents, sweeteners including artificial sweeteners and intense sweeteners may also be present in the composition according to the invention.

Preparation of an at Least Partly Film-Coated Calcium-Containing Compound, Combination or Composition of the Invention and of Pharmaceutical Compositions Containing Such Calcium-Containing Compounds, Combinations and Compositions The present invention also provides a method for the preparation of an at least partly film-coated calcium-containing compound according to the invention, the method comprising applying a coating composition comprising one or more water-soluble substances and one or more polymeric substances on a calcium-containing compound. To this end, it is important to note that in order to obtain satisfactory results, the coating composition and/or granulation liquid employed contains a mixture or a solution of the two components. When applied in one and the same coating composition or granulation liquid, the synergistic effect is achieved and this enables the preparation of very small Ca-containing tablets with suitable properties. As mentioned herein before, the two components are notably water-soluble to provide a water-soluble film and are normally dissolved in an aqueous medium, notably water, before application. As seen from the Examples herein, the coating composition or granulation liquid may also contain other substances such as, e.g., an artificial sweetener.

Normally, the water-soluble substance and the polymeric substance is dispersed or dissolved in a solvent such as an aqueous or an organic solvent. In a specific embodiment, the solvent is an aqueous solvent.

As mentioned herein before, one ore more active substances, one or more pharmaceutically acceptable excipients and/or one or more additives may be contained in the coating composition. In one embodiment sweeteners including intense sweeteners, colors, aromas, acidulents, flavors or the like is added to the solvent.

In general, the application of the coating composition is performed by spraying, melting or spray drying by use of fluid bed, spray drying, melt granulation, extrusion, high shear mixing, or rotoprocessing.

Embodiments Relating to Fluid Bed Processing

As it appears from the Examples herein, specific embodiment relates to a method, wherein the coating composition is applied by use of fluid bed.

To this end the following has been observed:

The compositions according to the invention are made by top spray fluid bed coating and agglomeration in a Glatt GPCG 3 pilot scale model with the general set points for the processing parameters as follows:

| | |
|---|---|
| Batch size: | 3-5 kg (3-3.5 kg) |
| Granulation inlet temperature: | 45-90° C. (45 and 80° C.) |
| Granulation liquid amount: | 200-800 gram (200-400 gram) |
| Spray rate: | 40-120 g/min (40-100 g/min) |
| Spray atomizing pressure: | 1.5 bar |
| Drying inlet temperature: | 80-90° C. (80° C.) |
| Endpoint temperature drying: | 45° C. |
| Endpoint temperature cooling: | 42° C. |

Scoralite 1B from Scora Watrigant SA, France has been used in al the trials unless otherwise stated.

In cases where a soluble filler (water-soluble substance) has been added to the dry calcium-containing compound before processing in the fluid bed then the polyol or carbohydrate has been sieved at 210 μm (70 mesh). Alternatively the soluble filler can be milled in order to break up lumps and agglomerates. Powder blends of calcium carbonate and xylitol were mixed in a Kenwood Major with a mixing intensity of 4 for 2 min before transfer to the GPCG 3 fluid bed.

The fluid bed granulates after fluid bed processing were screened at 1.4 mm (12 mesh) before bending with flavour granulate and magnesium stearate and finally tabletting with 14 mm normal concave punches.

The quality of calcium carbonate employed in all trials was Scoralite 1B or Scoralite 1B mainstream if not otherwise specified. This quality is suitable for fluid bed fluidization and coating as it consists of discrete cubic or pseudo-cubic shaped crystals with a particle size in the range of 5-20 μm and with a low value for the specific surface area in the range of 0.2 to 0.6 $g/m^2$. Specific examples can be found under the heading "Calcium carbonate" and in the examples herein.

The invention involves the coating and agglomeration of particles or crystals of the calcium-containing compound. The coating consists of a highly soluble film at least partly covering the surfaces of the calcium-containing compound as depicted in FIG. 1. FIG. 1A depicts at least partly film coated and agglomerated calcium carbonate crystals according to example 1 in the invention. Calcium carbonate alone without any added filer excipients has here been coated and agglomerated with a coating solution consisting of copovidone (e.g. PVP VA64) and xylitol. The picture with magnification 1500× indicates at least partly a coating on the calcium carbonate crystals.

Figure 7A:
FIGS. 7A and B show SEM photographs of submicron particles at magnifications of 1500× and 5000×.
Figure 7B:
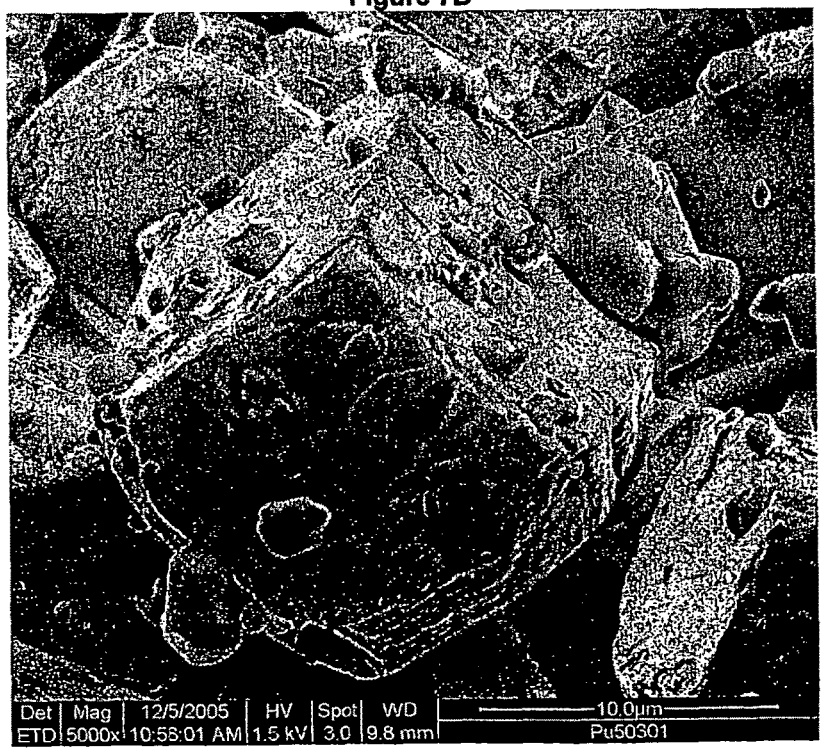

The granulate contains very little fines and granules up to 400 μm in size can be seen from the picture. Submicron particles can be seen to be embedded or fixated on to the crystal or particle surfaces of calcium carbonate. The chemistry of the embedded submicron particles was checked by energy dispersive spectroscopy during the SEM photography. The analysis revealed that the submicron particles had a higher carbon density compared to an average reading from a larger surface area which included the surfaces between the submicron particles. The submicron particles were also seen to melt at higher magnifications due to the heat generated from the electron beam in the microscope. FIGS. 7A and B which show SEM photograps at magnifications of 1500 and 5000×.

FIG. 1B depicts a granulate according to European application EP-A-1128815 of Nycomed Pharma consisting of calcium carbonate (74.5%), sorbitol (23.3%) and copovidone (2.2%) where a 28% solution of copovidone has been employed during the granulation step in a pilot scale Glatt GPCG 3 fluid bed. The binding mechanism can be seen in the form of a fine network or mesh consisting of PVP VA64, which binds the calcium carbonate crystals together. A considerable amount of fine material from calcium carbonate can be seen together with the larger irregular sorbitol particles.

Thus, the employment of copovidone alone in the granulation liquid results in a different binding mechanism in the granules where there is no evidence of a coating effect taking place during the fluid bed granulation step. Also there is no evidence of embedded submicron particles on the crystal surfaces of calcium carbonate.

As mentioned herein before, the focus for the formulation work was to make a smaller and more compact chewable tablet or preferably a met formulation with very good sensory properties. The formulation should agglomerate well, compress well at low tabletting pressures to give rise to tablets with a low value for the friability below 2%.

A tablet weight of approximately 1400 mg comprising 1250 mg calcium carbonate and with a tablet diameter of 14 mm was aimed for.

Fluid bed granulation trials revealed that the composition of the granulation liquid (i.e. coating composition) was critical both in order to achieve a satisfactory agglomeration and also in order to facilitate a compression of tablets at low tabletting pressures which exhibited a low value for the friability below 2%. Unsuccessful agglomeration was the result when calcium carbonate alone without any excipients was granulated with a 28% solution of copovidone or with a 50% solution of xylitol. Unsuccessful tablet compression was likewise the result when tablets were made from these granulates.

Surprisingly, it was found that a synergistic effect appeared at two levels when povidone K30 or copovidone as examples of polymeric substance (with binding properties) were combined with xylitol as an example of the water-soluble substance (i.e. soluble filler material) in the granulation liquid (i.e. coating composition). Firstly, at the fluid bed granulation step a very rapid agglomeration was achieved with very little fine material and with narrow particle size distributions as follows:

D (v, 0.1)=30-90 µm
D (v, 0.5)=130-350 µm
D (v, 0.9)=280-800 µm

The particle size analysis was performed on a Malvern Mastersizer S long bench apparatus where D(v, 0.1), D(v, 0.5) and D(v, 0.9) give the particle sizes for which 10%, 50% and 90% of the particles by volume have sizes below the given values.

The narrow particle size distributions achieved in the entailed examples were characterized by a low span value below 2.0. The span value is calculated as [D(v, 0.9)–D(v, 0.1)/D(v, 0.5). A narrow size distribution and a mean particle size which coincides with the mean particle size and particle size distribution of vitamin $D_3$ has been found to be important in order to ensure a satisfactory homogeneity of vitamin $D_3$ in the secondary granulate or the tableting end-mix in the case it is desired to incorporate vitamin D into the tablets.

Secondly, a synergistic effect was seen when granulates based on the combination of a polymeric binder and a soluble filer in the granulation liquid were compressed into tablets. Very good compression curves were achieved as opposed to formulations were only one of the components had been used in the granulation liquid.

Compression Curves

The compression curves were carried out on a rotary tabletting machine (Manesty B3B), which was instrumented with a compaction force monitor in order to measure the tabletting pressures. Tablet compression curves were drawn by plotting the crushing strength in Newton (N) against the corresponding tabletting pressure in kilo Newton (kN). The mean crushing strength from five tablets was measured at tabletting pressures of 10, 14, 18, 22 and 26 kN.

A satisfactory compression curve was characterized by a linear curve over the whole range of tabletting pressures and that tablets with a satisfactory crushing strength and friability could be produced at low tabletting pressures. A number of formulations described in the entailed examples achieved this with crushing strengths in the range of 30-60 N and with friability values below 2% for tablets produced at low tabletting pressures of 6 to 14 kN.

Sensory Evaluation of Calcium Tablet Formulations

The sensory panel consisted of seven selected assessors and was used in order to detect differences between chewable and melt tablet formulations with respect to lemon flavor intensity, solubility of the tablet in the mouth and adhesiveness or stickiness of tablet residues in the teeth. The intensity of each attitude was characterized by plotting the score on a visual-analogue scale. The tests were carried out in a sensory laboratory in controlled environments. Each assessment of a particular sample was carried out twice by each assessor.

Statistical differences were detected by employing ANOVA with 95% confidence level and Tukey's HSD test with a significance level of 5% to discriminate among means. Registration of data and statistical analysis were carried out by employing Compusense 4.0 and Statgraphics 4.0, respectively.

Two compostions according to the invention were tested on all three parameters against two reference or comparative examples. The two reference examples were based on two commercial qualities of directly compressible calcium carbonate, which were claimed to have improved sensory qualities when incorporated into chewable tablets. The results have been depicted in FIG. 5, which shows the results from the sensory analysis of example 3 and 4 according to the invention and reference example 3 and 4.

The two examples according to the invention came out statistically significant different when compared to the two reference examples with respect to an increased lemon flavor intensity, more soluble and reduced adhesiveness in the mouth.

Definition of Selected Terms Use Herein

The term "coated" is intended to mean a homogenous layer which at least partly covers the individual particle or crystal, which has been subjected to the coating and agglomeration process. A visual description of coated and agglomerated calcium carbonate crystals is given in figure A.

The term "particulate material" is intended to be synonymous with granulate material or simply granulate.

The term "formulated" is intended to relate to the selection of excipients, carriers, vehicles, solvents, co-solvents, preservatives, coloring agents, flavoring agents and so forth in the preparation of a medicament using said composition.

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical formulation, which has acceptable technical properties.

In the present context, the term "released" means dissolved, when referred to in relation to in vitro dissolution tests.

Calcium-Containing Compound

The calcium-containing compound contained in a particulate material made according to the invention is a physiologically tolerable cacium-containing compound that is therapeutically and/or prophylactically active.

Calcium is essential for a number of key functions in the body, both as ionized calcium and a calcium complex (Campell A K. Clin Sci 1987; 72:1-10). Cell behaviour and growth are regulated by calcium. In association with troponin, calcium controls muscle contraction and relaxation (Ebashi S. Proc R Soc Lond 1980; 207:259-86).

Calcium selected channels are a universal feature of the cell membrane and the electrical activity of nerve tissue and the discharge of neurosecretory granules are a function of the balance between intracellular and extra cellar calcium levels (Burgoyne R D. Biochim Biophys Acts 1984; 779: 201-16). The secretion of hormones and the activity of key enzymes and proteins are dependent on calcium. Finally calcium as a calcium phosphate complex confers rigidity and strength on the skeleton (Boskey A L. Springer, 1988: 171-26). Because bone contains over 99% of the total body calcium, skeletal calcium also serves as the major long-term calcium reservoir.

Calcium salts such as, e.g., calcium carbonate is used as a source of calcium especially for patients suffering from or at risk of osteoporosis. Moreover, calcium carbonate is used as an acid-neutralizing agent in antacid tablets.

As mentioned above, calcium has a number of important functions within the mammalian body in particular in humans. Furthermore, in many animal models, chronic low calcium intake produces osteopenia. The osteopenia affects cancellous bone more than cortical bone and may not be completely reversible with calcium supplementation. If the animal is growing reduced calcium intake leads to stunting. In the premature human neonate the higher the calcium intake, the greater the increase in skeletal calcium accretion which, if high enough, can equal gestational calcium retention. During growth chronic calcium deficiency causes rickets. Calcium supplements in both pre- and postpubertal healthy children leads to increased bone mass. In adolescents the higher the calcium intake, the greater the calcium retention, with the highest retention occurring just after menarche. Taken together, these data suggest that in children and adolescents considered to be taking an adequate intake of calcium, peak bone mass can be optimized by supplementing the diet with calcium. The mechanisms involved in optimizing deposition of calcium in the skeleton during growth are unknown. They are probably innate properties of the mineralization process that ensures optimal calcification of the osteoid if calcium supplies are high. The factors responsible for stunting of growth in states of calcium deficiency are also unknown but clearly involve growth factors regulating skeletal size.

In adults calcium supplementation reduces the rate of age-related bone loss (Dawson-Hughes B. Am J Clin Nut 1991; 54:S274-80). Calcium supplements are important for individuals who cannot or will nor achieve optimal calcium intakes from food. Furthermore, calcium supplement is important in the prevention and treatment of osteoporosis etc.

Furthermore, calcium may have anticancer actions within the colon. Several preliminary studies have shown high calcium diets or intake of calcium supplementation is associated with reduced colon rectal cancer. There is increasing evidence that calcium in combination with acetylsalicylic acid (ASA) and other non-steroidal anti-inflammatory drugs (NSAIDS) reduce the risk the risk of colorectal cancer.

Recent research studies suggest that calcium might relieve premenstrual syndrome (PMS). Some researchers believe that disruptions in calcium regulation are an underlying factor in the development of PMS symptoms. In one study, half the women of a 48 person group of pre-menopausal women from across the U.S. were tracked for three menstrual cycles and were given 1200 mg of calcium supplements daily throughout the cycle. The final results showed that 48% of the women who took placebo had PMS related symptoms. Only 30% of those receiving calcium tablets did.

Calcium salts like e.g. calcium carbonate is used in tablets and due to the high dose of calcium required, such tablets are often in the form of chewable tablets. It is a challenge to formulate e.g. chewable tablets containing a calcium salt, which tablets have a pleasant taste and an acceptable mouth feel without the characteristic dominating taste or feeling of chalk.

A calcium-containing compound for use according to the invention may be e.g. bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate, or mixtures thereof. Other calcium sources may be water-soluble calcium salts, or complexes like e.g. calcium alginate, calcium-EDTA and the like or organic compounds containing calcium like e.g. calcium organophosphates. Use of bone meal, dolomite and other unrefined calcium sources is discouraged because these sources may contain lead and other toxic contaminants. However, such sources may be relevant if they are purified to a desired degree.

The calcium-containing compound may be used alone or in combination with other calcium-containing compounds.

Of specific interest is bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Mixtures of different calcium-containing compounds may also be used. As appears from the examples herein, calcium carbonate is especially suitable for use as a calcium-containing compound and calcium carbonate has a high content of calcium.

Of particular interest is calcium carbonate.

Normally, a tablet made according to the invention contains an amount of the calcium-containing compound corresponding to from about 100 to about 1000 mg Ca such as, e.g., from about 150 to about 800 mg, from about 200 to about 700 mg, from about 200 to about 600 mg or from about 200 to about 500 mg Ca.

Calcium Carbonate

Calcium carbonate can be in three different crystal structures: calcite, aragonite and vaterite. Mineralogically, these are specific mineral phases, which relate to the distinct arrangement of the calcium, carbon and oxygen atoms in the crystal structure. These distinct phases influence the shape and symmetry of the crystal forms. For example, calcite is available in four different shapes: scalenohedral, prismatic, spherical and rhombohedral, and aragonit crystals can be obtained as e.g. discrete or clustered needle-like shapes. Other shapes are also available such as, e.g., cubic shapes (Scoralite 1A+B from Scora).

As shown in the examples herein, a particular suitable quality of calcium carbonate is calcium carbonate having a mean particle size of 60 μm or less such as, e.g., 50 μm or less or 40 μm or less.

Furthermore, an interesting quality of calcium carbonate has a bulk density below 2 g/mL Calcium carbonate 2064 Merck (available from Merck, Darmstadt, Germany) that has a mean particle size of 10-30 μm, an apparent bulk density of 0.4 to 0.7 g/mL, and a specific surface area of 0.3 $m^2/g$;

Calcium carbonate 2069 Merck (available from Merck, Darmstadt, Germany) that has a mean particle size of approx. 3.9 μm, and an apparent bulk density of 0.4 to 0.7 g/mL;

Scoralite 1A (available from Scora Watrigant SA, France) has a mean particle size of 5 to 20 μm, an apparent bulk density of 0.7 to 1.0 g/mL, and a specific surface area of 0.6 $m^2/g$;

Scoralite 1B (available from Score Watrigant SA, France) has a mean particle size of 10-25 μm, an apparent bulk density of 0.9 to 1.2 g/mL, and a specific surface area of 0.4 to 0.6 $m^2/g$;

Scoralite 1A+B (available from Scora Watrigant SA, France) have a mean particle size of 7-25 μm, an apparent bulk density of 0.7 to 1.2 g/mL, and a specific surface area of 0.35 to 0.8 $m^2/g$;

Pharmacarb LL (available from Chr. Hansen, Mahawah New Jersie) L has a mean particle size of 12-16 μm, an apparent bulk density of 1.0 to 1.5 g/mL, and a specific surface area of 0.7 $m^2/g$;

Sturcal H has a mean particle size of approx. 4 μm, an apparent bulk density of 0.48 to 0.61 g/mL;

Sturcal F has a mean particle size of approx. 2.5 μm, an apparent bulk density of 0.32 to 0.43 g/mL;

Sturcal M has a mean particle size of 7 μm, an apparent bulk density of 0.7 to 1.0 g/mL, and a specific surface area of 1.5 $m^2/g$;

Mikhart 10, SPL, 15, 40 and 65 (available from Provencale, Provencale, France);

Mikhart 10 has a mean particle size of 10 μm,

Mikhart SPL has a mean particle size of 20 μm,

Mikhart 15 has a mean particle size of 17 μm,

Mikhart 40 has a mean particle size of 30 μm, an apparent bulk density of 1.1 to 1.5 g/mL;

Mikhart 65 has a mean particle size of 60 μm, an apparent bulk density of 1.25 to 1.7 g/mL;

Hubercal Elite 500 (available from J. M. Huber Corp., USA) has a mean particle size of 5.8 μm and a specific surface area of 1.8 $m^2m^2/g$;

Hubercal Bite 500 (available from J. M. Huber Corp., USA) has a mean particle size of 8.2 μm and a specific surface area of 1.3 $m^2/g$.

Omyapure 35, (available from Omya S. A. S, Paris, France) has a mean particle size of 5-30 μm, and a specific surface area of 2.9 $m^2/g$;

Socal P2PHV (available from Solvay, Brussels, Belgium) has a mean particle she of 1.5 μm, an apparent bulk density of 0.28 g/mL, and a specific surface area of 7.0 $m^2/g$;

Calci Pure 250 Heavy, Calci Pure 250 Extra Heavy and Calci Pure GCC HD 212 with a mean particle size of 10-30 μm, an apparent bulk density of 0.9-1.2 g/ml, and a specific surface area of 0.7 $m^2/g$ (available from Particle Dynamic Inc., St. Louis Mont.).

The content of the calcium-containing compound in a tablet made according to the present invention is in a range from about 40% to about 100% w/w such as, e.g., from about 45% to about 98% w/w, from about 50% to about 95% w/w, from about 55% to about 90% w/w or at least about 60% w/w, at least about 65% w/w, at least about 70% w/w, at least about 75% w/w, at least about 80% w/w or at least about 85% w/w.

Normally, the dose of calcium for therapeutic or prophylactic purposes is from about 350 mg (e.g. newborn) to about 1200 mg (lactating women) daily. The amount of the calcium-containing compound in the tablets can be adjusted to that the tablets are suitable for administration 1-4 times daily, preferably once or twice daily.

As mentioned above, the granulate obtained by the method according to the invention may be used as such, but it is also very suitable for further manufacturing into solid dosage forms like e.g. tablets, capsules or sachets.

A person skilled in the art will know how to adjust the composition and the various process parameters in order to obtain a desired calcium-containing product.

In one embodiment of the invention, the granulate obtained by the present method is intended to be manufactured into tablets. Often it is necessary to add one or more pharmaceutically acceptable excipients (e.g. lubricants) in order to avoid adherence and/or increase flowability of the granulate obtained. Accordingly, the method may also comprise a step of mixing the granulate obtained with one or more pharmaceutically acceptable excipients.

In the event that it is desired to include other active substances than the calcium-containing compound, the method may also comprise a step of adding one or more therapeutically, prophylactically and/or diagnostically active substance to the granulate obtained.

Such substances include one or more nutrients such as, e.g., one or more vitamins or minerals. In a specific embodiment, the further active substance is a D-vitamin such as, e.g., $D_3$ vitamin, $D_2$ vitamin or derivatives thereof.

D Vitamin or Other Active Substances

A particulate material as well as a tablet obtained according to the invention may comprise a further therapeutically and/or prophylactically active substance. Of particular interest are one or more D-vitamin compounds. Non-limiting examples are dry vitamin D3, 100 CWS available from Roche and dry vitamin D3 100 GFP available from BASF.

A particulate material or tablet made according to the invention may comprise a further therapeutically and/or prophylactically active substance, or it may contain one or more nutrients such as, e.g. one or more vitamins or minerals. Of specific interest are e.g. vitamin B, vitamin C, vitamin D and/or vitamin K, and derivatives thereof, and minerals like e.g. zinc, magnesium, selenium etc.

Of particular interest are one or more D-vitamin compounds such as, e.g., Vitamin $D_2$ (ergocalciferol) and Vitamin $D_3$ (cholecalciferol) including dry vitamin $D_3$, 100 CWS available from Roche and dry vitamin $D_3$ 100 GFP available from BASF.

In addition to its action on calcium and skeletal homeostasis, vitamin D is involved in the regulation of several major systems in the body. The actions of vitamin D are medicated at the genome by a complex formed by 1,25-$(OH)_2$ vitamin D mainly produced in the kidney, with the vitamin D receptor (VDR). The latter is widely distributed in many cell types. The 1,25-$(OH)_2$ vitamin D/VDR complex has important regulatory roles in cell differentiation and in the immune system. Some of these actions are probably dependant on the ability of certain tissues other than the kidney to produce 1,25-$(OH)_2$ vitamin D locally and act as a paracrine (Adams J S et al. Endocrinology 1996; 137: 4514-7).

In humans, deficiency of vitamin D results in rickets in children and osteomalacia in adults. The basic abnormality is a delay in the rate of mineralization off osteoid as it is laid down by the osteoblast (Peacock M. London Livingstone, 1993:83-118). It is not clear whether this delay is due to a failure of a 1,25-$(OH)_2$ vitamin D-dependant mechanism in the osteoblast or to reduced supplies of calcium and phosphate secondary to malabsorption or a combination of both. Accompanying the mineralization delay, there is reduced supply of calcium and phosphate, severe secondary hyperparathyroidism with hypocalcemia and hypophosphatemia and increased bone turnover.

Vitamin D insufficiency, the preclinical phase of vitamin D deficiency, also causes a reduced calcium supply and secondary hyperparathyroidism, albeit of a milder degree than found with deficiency. If this state remains chronic, osteopenia results. The biochemical process underlying this state of calcium insufficiency is probably inappropriate level of 1,25-$(OH)_2$ vitamin D due to a reduction in its substrate 25-OHD (Francis R M et al. Eur J Cin Invest 1983; 13:391-6). The state of vitamin D insufficiency is most commonly found in the elderly. With age there is a decrease in serum 25-OH vitamin D due to decreased sunlight exposure and possible to decreased skin synthesis. Furthermore, in the elderly the condition is exacerbated by a decrease in calcium intake and a paradoxical decrease in calcium absorption. The reduction in renal function with age giving rise to reduced renal 1,25-$(OH)_2$ vitamin D production may be a contributing factor. There are a number of studies of the effects of vitamin D supplementation on bone loss in the elderly. Some are without calcium supplementation and others are with calcium supplementation. It appears from the studies that although vitamin D supplementation is necessary to reverse deficiency and insufficiency, it is even more important as far as the skeleton is concerned to provide calcium supplementation since the major skeletal defect is calcium deficiency. In literature based on clinical trials, recent finding suggest trends of need for higher doses of vitamin D for the elderly patients (Compston J E. BMJ 1998; 317:1486-67). An open quasi-randomised study of annual injections of 150.000-300.000 IU of vitamin D (corresponding to approx. 400-800 IU/day) showed a significant reduction in overall fracture rate but not in the rate of hip fracture in treated patients (Helkinheimo R J et al. Calcif Tissue Int 1992; 51:105-110).

As it appears from above, a combination of calcium and vitamin D is of interest. The recommended Dally Allowance (RDA) of calcium and vitamin $D_3$ are as follows (European Commission. Report on osteoporosis in the European Community. Action for prevention. Office for official Publications of the European Communities, Luxembourg 1998):

| Group | Age (years) | Calcium (mg)* | Vitamin $D_3$ (µg) |
|---|---|---|---|
| Newborn | 0-0.5 | 400 | 10-25 |
| | 0.5-1.0 | 360-400 | 10-25 |
| Children | 1.0-3.0 | 400-600 | 10 |
| | 4.0-7.0 | 450-600 | 0-10 |
| | 8.0-10 | 550-700 | 0-10 |
| Men | 11-17 | 900-1000 | 0-10 |
| | 18-24 | 900-1000 | 0-15 |
| | 25-65 | 700-800 | 0-10 |
| | 65+ | 700-800 | 10 |
| Women | 11-17 | 900-1000 | 0-15 |
| | 18-24 | 900-1000 | 0-10 |
| | 25-50 | 700-800 | 0-10 |
| | 51-65 | 800 | 0-10 |
| | 65+ | 700-800 | 10 |
| Pregnant | | 700-900 | 10 |
| Lactating | | 1200 | 10 |

*RDA of calcium varies from country to country and is being re-evaluated in many countries.

Vitamin D is very sensitive towards humidity and is subject to degradation. Therefore, vitamin D is often administered in a protective matrix. Accordingly, when tablets are prepared containing a vitamin D it is of utmost importance that the compression forces applied during the tabletting step do not decrease the protective effect of the matrix and thereby impair the stability of vitamin D. To this end, the combination of the various ingredients in a granulate or tablet made according to the invention has proved to be very suitable in those cases where vitamin D also is incorporated into the composition as it is possible to employ a relatively low compression force during tableting and still achieve a tablet with suitable mechanical strength (crushing strength, friability etc.).

In a specific embodiment, the invention provides a tablet comprising
i) a calcium-containing compound as an active substance,
ii) a vitamin D, and
iii) optionally one or more pharmaceutically acceptable excipients or actives.

More specifically, the tablet may comprise
i) at least 200 mg of the calcium-containing compound (normal range 200-1500 mg),
ii) at least 5 µg of vitamin D (normal range 5-100 µg-1 µg=40 IU), and
iii) optionally one or more pharmaceutically acceptable excipients or actives.

In a specific embodiment, the invention provides a tablet comprising
i) from about 50% to about 90% w/w of the calcium-containing compound,
ii) from about 0.00029% about 0.0122% w/w of a vitamin D, and
iii) optionally one or more pharmaceutically acceptable excipients or actives with the proviso that the total amount of ingredients corresponds to about 100% w/w.

In particular, the tablet may comprise
i) from about 50% to about 90% w/w of the calcium-containing compound,
ii) from about 5 to about 40% w/w of a sweetening agent,
iii) from about 0.12% to about 4.9% w/w of a vitamin D including a protective matrix,
iv) optionally one or more pharmaceutically acceptable excipients or actives with the proviso that the total amount of ingredients corresponds to about 100% w/w.

Other Active Ingredients

Examples include isoflavones, vitamin K, vitamin C, vitamin B6 and oligosaccharides such as inulin and oligofructose. Isoflavones exhibit a weak oestrogenic effect and can thus Increase bone density in post-menopausal women. Isoflavones are available under the trade name Novasoy 400 from ADM Nutraceutical, Illinois, USA. Novasoy 400 contains 40% isoflavones and will typically be used in an amount sufficient to provide 25 to 100 mg isoflavone/dosage. Isoflavones may be included in the second granulate; however as Novasoy 400 is a relatively cohesive powder it is preferred that it be included in the first granulate in order to ensure that it is uniformly distributed. Vitamin K (more especially vitamin $K_1$) may improve biochemical markers of bone formation and bone density and low concentrations of vitamin K, have been associated with low bone mineral density and bone fractures. Vitamin K, is available from Roche as Dry Vitamin K, 5% SD, a dry substance containing 5% vitamin K1. Typically vitamin K, will be used in a quantity sufficient to provide 0.05 to 5 mg vitamin Kj/dosage. Vitamin C and vitamin 68 (available from Roche, Takeda and BASF amongst others) function as co-factors in the formation of collagen, the main component of the organic matrix of bone. Vitamin C and vitamin B6 will typically be used in quantities sufficient to provide 60 to 200 mg vitamin C/dosage and 1.6 to 4.8 mg vitamin B6/dosage respectively.

Oligosaccharides have been shown to facilitate and increase calcium absorption and may typically be used in quantities sufficient to provide 0.3 to 5 g oligosaccharide/dosage. In general it is desirable that a total of at least 5 g oligosaccharide is administered daily to facilitate calcium uptake and to obtain a prebiotic effect.

Where an active component is used which forms a minor part of the overall granulate, e.g. vitamin D, it is general preferred to produce a premix of such a component and the granulate before mixing the premix and the remaining required quantity of the granulate. This ensures uniform distribution of the minor component in the granulate.

Pharmaceutically Acceptable Excipients

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical composition, which has acceptable technical properties.

The calcium-containing compound is normally admixed with one or more pharmaceutically acceptable excipients before compression into tablets. Such excipients include those normally used in formulation of sold dosage forms such as, e.g. filers, binders, disintegrants, lubricants, flavoring agents, coloring agents., including sweeteners, pH adjusting agents, buffering agents, stabilizing agents, etc.

In the following are given examples of excipients suitable for use in a tablet according to the present invention.

| Excipient | Concentration [% w/w of formulation] |
|---|---|
| Sweetening agents | If present, max 20 (3-40) |
| Artificial sweeteners | If present, max 0.3 (0.02-0.3) |
| Flavors | If present, max 3 (0.1-3) |
| Disintegrating agents | 0.5-5 |
| Glidants and lubricants | 0.1-5 |
| Fillers/diluents/binders including water-soluble substance | 0.1-20 (0.1-15) |

-continued

| Excipient | Concentration [% w/w of formulation] |
|---|---|
| Film-forming agents (polymeric substances) | 0.1-5 |
| Film additives | If present, max 5 (0.05-5) |

Sweetening Agents

Examples of suitable sweeteners include dextrose, erythritol, fructose, glycerine, glucose, inositol, isomalt isomaltulose, lacitol, lactose, maltitol, maltose, mannitol, sorbitol, sucrose, tagatose, trehalose, xylitol, etc. Sorbitols e.g. Neosorb P100T, Sorbidex P166B0 and Sorbogem Fines Crystalline Sorbitol available from Roquette Freres, Cerestar and SPI Polyols Inc. respectively. Maltisorb P90 (maltitol) available from Roquette Freres, Xylitol CM50, Fructofin CM (fructose) and Lactitol CM50 available from Danisco Sweeteners, Isomalt ST-PF and palatinose (isomaltulose), Gaio Tagatose and Mannitol available from Palatinit, Aria Foods and Roquette, Freres respectively. Sorbitol has a sweetening effect (compared to sucrose) of 0.55; maltitol that has a sweetening effect of ≥1; xylitol that has a sweetening effect of 1, isomalt that has a sweetening effect of >0.5, etc. The sweetening effect may be of value in connection with choosing the individual sweetening agents. Thus, if a decreased tablet weight and volume are desired, it is suitable to choose a sweetening agent having a high sweetening effect.

Artificial Sweeteners

Acesulfam potassium, alitame, aspartame, cyclamic acid, cyclamate salt (e.g. calcium cyclamate, sodium cyclamate), neohesperidine dihydrochalcone, neohesperidine hydrochloride, saccharin, saccharin salt (e.g. ammonium saccharin, calcium saccharin, potassium saccharin, sodium saccharin), sucralose, taumatin and mixtures thereof.

Flavours

Apricot, Lemon, Lemon/Lime, Lime, Orange, Mandarine, such as Apricot 501.110 AP0551, Lemon 501.051 TP0551, Lemon 501.162 AP0551, Lemon/Lime 501.053 TP0551, Lime 501.054 TP0551, Orange 501.071 AP0551, Orange TP0551, Orange 501.434 P0551, Mandarine 501.AP0551, Lemon Durarome 501.282 TDI1091 available from Firmenich, Kerpen, Germany or Juicy Lemon Flavouring T3602 available from TasteTech, Bristol, England or Lemon Lime Flavour Permseal 11029-31, Lemon Flavour Permaseal 12028-31, Lemon Flavour Ultradseal 96918-71 Available from Givaudan Schweiz AG, Kemptthal, Schweiz or Lemon Flavour Powder 605786, Lemon Flavour Powder 605897 available from Frey+Lau Gmbh, Henstedt-Ulzburg, Germany Disintegrating Agents Alginic acid—alginates, carboxymethylcellulose calcium, carboxymethylcellulose sodium, crospovidone, hydroxypropylcellulose, hydroxypropylmethylcellulose (HPMC), cellulose derivatives such as low-substituted hydroxypropylcellulose (e.g LH 11, LH 20, LH 21, LH 22, LH 30, LH 31, LH 32 available from Shin-Etsu Chemical Co.) and microcrystalline cellulose, polacrilin potassium or sodium, polyacrylic acid, polycarbofil, polyethylene glycol, polyvinylacetate, polyvinylpyrrolidone (e.g. Polyvidon® CL, Polyvidon® CL-M, Colliding® CL, Polyplasdone® XL, Polyplasdone® XL-10); sodium carboxymethyl starch (e.g. Primo-gel® and Explotab®), sodium croscarmellose (i.e. cross-linked carboxymethylcellulose sodium salt; e.g. Ac-Di-Sol®), sodium starch glycolate, starches (e.g potato starch, maize starch, rice starch), pregelatinised starch.

Those skilled in the art will appreciate that it is desirable for compressible tablets to disintegrate within 30 minutes, more desirable within 15 min, most desirable within 5 min; therefore, the disintegrant used preferably results in the disintegration of the tablet within 30 minutes, more preferable within 15 min, most preferable within 5 min.

Effervescent agent (e.g. mixture of sodium hydrogen carbonate (carbonates, alkaline, alkaline earth metals) and citric acid (tartaric acid, fumaric add etc.)).

Glidants and Lubricants

Glidants and lubricants may be incorporated such as stearic acid, metallic stearates, talc, waxes and glycerides wt high melting temperatures, hydrogenated vegetable oils, colloidal silica, sodium stearyl fumarate, polyethylenglycols and alkyl sulphates.

Suitable lubricants include talc, magnesium stearate, calcium stearate, stearic acid, hydrogenated vegetable oils and the like. Preferably, magnesium stearate is used.

Fillers/Diluents/Binders

Dextrins, maltodextrins (e.g. Lodex® 5 and Lodex® 10), dextrose, fructose, glucose, inositol, erythritol, isomalt, lactitol, lactose (e.g., spray-dried lactose, α-lactose, β-lactose, Tabletose®, various grades of Pharmatose®, Microtose or Fast-Floc®), maltitol, maltose, mannitol, sorbitol, sucrose, tagatose, trehalose, xylitol, low-substituted hydroxypropylcellulose (e.g LH 11, LH 20, LH 21, LH 22, LH 30, LH 31, LH 32 available from Shin-Etsu Chemical Co.), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), starches or modified starches (e.g potato starch, make starch, rice starch, pre-gelatinised starch), polyvinylpyrrolidone (e.g. Kollidon 25, 30 and 90F from BASF and Plasdone K-12, K17, K-25, K-30 and K-90 from ISP), copovidone which is a polyvinylpyrrolidone/vinyl acetate copolymer (e.g. PVP VA64 from BASF and Plasdone S-630 from ISP), agar (e.g. sodium alginate), calcium hydrogen phosphate, calcium phosphate (e.g. basic calcium phosphate, calcium hydrogen phosphate), calcium sulphate, carboxyalkylcellulose, dextrates, dibasic calcium phosphate, gelatine, gummi arabicum, hydroxypropyl cellulose, hydroxypropylmethylcellulose, magnesium carbonate, magnesium chloride, methylcellulose, polyethylene glycol, polyethylene oxide, polysaccharides e.g. dextran, soy polysaccharide, sodium carbonate, sodium chloride, sodium phosphate.

Some of the above-mentioned substances also belong to the group of polymeric substances suitable for use according to the invention (see also the paragraph below). In particular, this applies to starches or modified starches (e.g potato starch, maize starch, rice starch, pre-gelatinised starch), polyvinylpyrrolidone, copovidone or polyvinylpyrrolidone/ vinyl acetate copolymer, agar (e.g. sodium alginate and polyetylene glycol alginate), carboxyalkylcellulose, gelatine, gummi arabicum, hydroxypropyl cellulose, hydroxypropylmethylcellulose, polysaccharides e.g. inulin, dextran, soy polysaccharide.

Surfactants/Enhancers

Surfactants may be employed such as

Non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitan monoisostearate, sorbitan monolaurate, sorbitan monopalmitate, sorbitan monostearate, sorbitan monooleate, sorbitan sesquioleate, sorbitan trioleate, glyceryl monooleate and polyvinylalkohol), anionic (e.g., docusate sodium and sodium lauryl sulphate)

cationic (e.g., benzalkonium chloride, benzethonium chloride and cetrimide)

Fatty adds, fatty alcohols and fatty esters, for example:
ethyl oleate, sodium oleate, lauric acid, methyl laurate, oleic acid, sodium caprate Dioctyl calcium sulfosuccinate, dioctyl potassium sulfosuccinate, dodecyltrmethylammonium bromide, cymonium bromide, trimethyltetradecylammonium bromide, polyoxyehtylene ethers (polyoxyehtylene-9-lauryl ether, sodium dodecyl sulphate, sodium dioctyl sulfosuccinate, sodium laurate, sodium 5-methoxysalicylate, sodium salicylate;

bile salts, for example:
sodium deoxycholate, deoxycholic acid, sodium cholate, cholic acid, sodium glycocholate, sodium glycodeoxycholat, sodium taurocholate, sodium tauodeoxycholate;

cytoadhesives, for example:
lectins (e.g. Lycopersicon Esculentum Agglutinin, Wheat Germ Agglutinin, Urtica Dioca Agglutinin).

N-acylated amino acids (especially N-[8-(2-hydroxy-4-methoxy)benzoyl]amino caprylic acid (4-MOAC), 4-[4-(2-hydroxybenzoyl)amino]butyric acid, sodium N-[8-(2-hydroxybenzoyl)amino]-caprylate);

phospholipids, for example:
hexadecylphosphocholine dimyristoylphosphatidylglycerol, lysophosphatidylglycerol, phosphatidylinositol, 1,2-di(2, 4-octadecadienoyl)-sn-glycerol-3-phosphorylcholine and phosphatidylcholines (e.g. didecanoyl-L-phosphatidylcholine, dilauroylphosphatidylcholine, dipalmitoylphosphatidylcholine, distearoylphosphatidylcholine), lysophosphatidylcholine is of particular interest cyclodextrins, for example:
β-cyclodextrin, dimethyl-γ-cyclodextrin, γ-cyclodextrin, hydroxypropyl β-cyclodextrin, methyl cyclodextrin; especially dimethyl-β-cyclodextrin is of particular interest;

fusidic acid derivatives, for example:
sodium taurodihydrofusidate, sodium glycodihydrofusidate, sodium phosphate-dihydrofusidate; especially sodium taurodihydrofusidate is of particulars interest;

others:
sodium salts of e.g. glycyrrhizic acid, capric acid, alkanes (e.g. azacycloalkanes), amines and amides (e.g. N-methyl-pyrrolidone, Azone), amino acids and modified amino acids compounds (e.g. acetyl-L-cysteine), polyols (e.g. propyleneglycol, hydrogels), sulfoxides (e.g. dimethylsulfoxide), terpenes (e.g. carvone), ammonium glycyrrizinate, hyluronic acid, isopropyl myristate, n-lauryl-beta-D-maltopyranoside, saponins, DL-octanonylcarnitine chloride, palmitoyl-DL-carnitine chloride, DL-stearoylcarnitine chloride, acylcarnitines, ethylenediaminedihydro-chloride, phosphate-dihydrofusidate, sodium CAP); especially n-lauryl-beta-D-maltopyranoside is of particular interest, alpha 1000 peptide, peptide MW<1000 comprising at least 6 mol % of aspertatic- and glutamic Acid, decomposed royal jelly, probiotica, butyrate, butyric acid, vitamin $D_2$, vitamin $D_3$, hydroxy-vitamin $D_3$, 1.25-dihydroxy-vitamin $D_3$, spirulina, proteoglycan, soyahydrolysate, lysin, lactic acid, di-fructose-anhydrid, vylitol Ca-(lactate), hydrolyzate of casein in particular a caseinoglycomacropeptide, negative ionization of $CaCO_3$, acetylsalicylic acid, vitamin K, creatin.

Film-Forming Agents (Polymer Substances)

Hydrofilic film formers such as polyvinylpyrrolidone, copovidone, hydroxypropylmethylcellulose (HPMC) (e.g. HPMC E5, HPMC E15), hydroxyethylcellulose, hydroxypropylcellulose, polydextrose and maltodextrin, Sepifilm™ and Sepifilm™ LP available from Seppic SA, Pharmacoat® available from Shin-Etsu Chemical Co.

Film Additives

Acetylated monoglyceride, acetyltributyl, acetyltributyl citrate, acetyltriethyl citrate, benzyl benzoate, calcium stearate, castor oil, cetanol, chlorobutanol, colloidal silica dioxide, dibutyl phthalate, dibutyl sebacate, diethyl oxalate, diethyl malate, diethyl maleate, diethyl malonate, diethyl fumarate, diethyl phthalate, diethyl sebacate, diethyl succinate, dimethylphthalate, dioctyl phthalate, glycerin, glyceroltributyrate, glyceroltriacetate, glyceryl behanate, glyceryl monostearate, hydrogenated vegetable oil, lecithin, leucine, magnesium silicate, magnesium stearate, polyethylene glycol, propylene, glycol, polysorbate, silicone, stearic acid, talc, titanium dioxide, triacetin, tributyl citrate, triethyl citrate, zinc stearate, wax.

The following non-limiting examples are meant to illustrate the present invention.

EXAMPLES

The examples were processed according to the entailed detailed description of the invention.

Fluid bed granulation and drying takes place in a fluid bed spray granulator consisting of a product container and an expansion chamber for fluidization of the powder mixture to be granulated. Details regarding the settings are mentioned herein before. The powder mixture is resting on a product screen at the bottom of the product container and restricted from escaping the expansion chamber by an exhaust filter on the outlet side of the fluid bed spray granulator. The airflow necessary for fluidization of the powders is generated by a suction fan mounted in the top portion of the unit. The air used for fluidization is heated to the desired temperature by an air heater positioned in the air inlet portion of the equipment. The powder mixture is fluidized by a sufficient air volume and the granulation liquid is atomized as a fine spray through a spray head consisting of a multiple of binary nozzles. The spray head may add the atomised spray of granulation liquid counter-current to the pulsating particles denoted "top spray" or co-current to the pulsating bed denoted "bottom spray". The wetted particles undergo agglomeration or granulation through particle—particle contacts. After appropriate agglomeration is achieved, the spray operation is discontinued and the material is dried and discharged from the unit. By adjusting the critical formulation characteristics and process parameters for the fluid bed process it is possible to agglomerate, instantize or coat individual particles in a powdery mixture.

Unless otherwise specified, the compositions were standardized with respect to tablet weight, concentration and type of intense sweetener, amount and type of flavor, amount of magnesium stearate and tabletting pressures employed in order to facilitate the comparison between the formulations. The tabletting pressure was adjusted in each case in order to obtain a satisfactory value for the friability below 2%.

Tablet compression curves were carried out for the majority of the formulations in order to investigate the compression behavior as a function of formulation variables e.g. type and amount of polymeric substance and water-soluble substance in the coating layer of the calcium carbonate crystals.

The water-soluble substance like xylitol and other polyols and carbohydrates was in the majority of the formulations divided in two amounts to the granulation liquid and dry powder mixture before fluid bed agglomeration and coating respectively.

The granulates and tablets were characterized with respect to bulk density, particle size and distribution, tabletting pressure, crushing strength, friability, tablet density, tablet porosity, disintegration and dissolution. Both disintegration and dissolution were carried out according to Ph. Eur. as described in the above text. The dissolution test was only carried out for example 1, 2, 3, 4, ref. Ex. 3 and ref. Ex. 4.

Examples 1, 2, Reference Examples 1 and 2

| Ingredient (mg) per tablet | Example. 1 | Example 2 | Reference example 1 | Reference example 2 |
|---|---|---|---|---|
| Calcium carbonate | 1250 | 1250 | 1250 | 1250 |
| Copovidone | 46.7 | 46.7 | 46.7 | |
| Inulin | | | | |
| Sucralose | 0.50 | 0.50 | 0.33 | 0.50 |
| Xylitol (gran. liquid) | 32.8 | 49.5 | | 83.00 |
| % binder* in gran. liq. | 28% | 28% | 28% | |
| % filler** in gran. liq. | 19.7 | 29.7 | | 49.8% |
| Wht. Gran. liq. | 400 | 400 | 400 | 400 |
| Xylitol (dry mixture) | | 53.3 | | 16.5 |
| Sorbitol | | | | |
| Dried granulate | 1330 | 1400 | 1297 | 1350 |
| Flavour granulate | 40.2 | 42.0 | 39.2 | 41.2 |
| Mg. stearate | 4.8 | 5 | 4.6 | 4.8 |
| Tablet weight | 1375 | 1447 | 1341 | 1396 |
| Characterization of Granulate: | | | | |
| Bulk density | 0.71 | 0.71 | 0.70 | 0.75 |
| Mavern $D_{10}$ (µm) | 82 | 67 | 25 | 26 |
| Malvern $D_{50}$ (µm) | 219 | 225 | 87 | 65 |
| Malvern $D_{90}$ (µm) | 460 | 530 | 214 | 154 |
| Span value | 1.10 | 2.06 | 2.17 | 1.97 |
| Characterization of tablet: | | | | |
| Tabletting pressure (kN) | 10 | 14 | 18 | Capping at all pressures |
| Tablet density (g/cm$^3$) | 1.60 | 1.56 | | |
| Tablet porosity (%) | 36.0 | 34.9 | | |
| Crushing strength (N) | 44 | 45 | 30 | |
| Friability (%) | 0.5 | 1.4 | 19 | 100 |
| Disintegration (min) | 3.40 | 3 | *** | *** |
| Hanging tablet slip time (sec) | 60 | 102 | *** | *** |
| Dissolution rate (10 min) | 90 | 91 | *** | *** |

*the term "binder" used in connection with the granulation liquid (or film-coating composition) is equivalent with the term "polymeric substance".
**the term "filler" used in connection with the granulation liquid (or film-coating composition) is equivalent with the term "water-soluble substance).
*** Tests not carried out due to faulty tablets Reference example 1 shows a formulation where a 28% solution of copovidone has been used as the granulation liquid during the fluid bed granulation and drying. The formulation did not agglomerate satisfactory resulting in a granulate with too much fine material and a low value for the mean particle size. Compressing the granulate into tablets at a high tabletting pressure of 18 kN proved difficult resulting in tablets with a too low crushing strength and very friable tablets with a too high value for the friability.

Granulating with a 50% solution of xylitol in reference example 2 resulted in a very poor granulate which did not compress at all and with a friability value of 100%

Example 1 according to the invention is calcium carbonate, which has been granulated without any added filer material and with a granulation liquid consisting of 28% copovidone and 19.7% xylitol. Surprisingly the combination of the polymeric binder material and soluble filler in the granulation liquid has resulted in a very good agglomeration with a high value of 82 µm for $D_{10}$ and a mean particle size of 219 µm for the granulate.

Example 2 according to the invention shows calcium carbonate with a small addition of xylitol to the powder mixture before fluid bed granulation and coating and where a granulation liquid consisting of 28% copovidone and 29.7% xylitol has been employed. A free-flowing granulate with little fine material and with a mean particle size of 225 µm was achieved.

Figure 3:
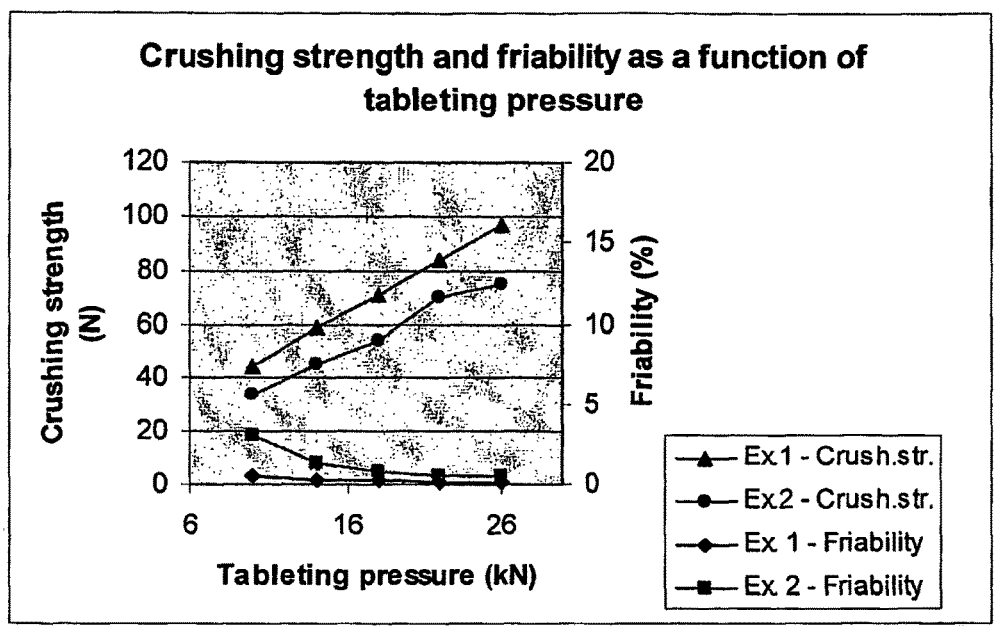
FIG. 3 illustrates tablet compression curves achieved for examples 1 and 2.
Figure 4:
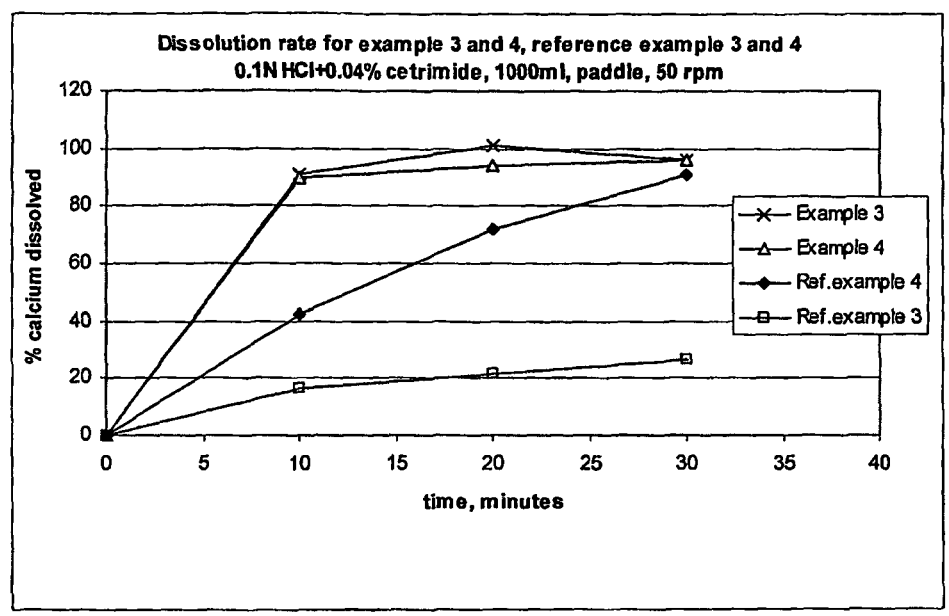
FIG. 4 illustrates the dissolution rate for examples 3 and 4.

Equal surprising is the very good tablet compression curves achieved for example 1 and 2 as shown in FIG. 3. Linear compression curves can be seen for the two examples with satisfactory friability values below 2% at low tabletting pressures in the range of 10 to 14 kN.

Tablet examples 1 and 2 are further characterized with a low values for the tablet densities giving rise to a small tablets where a satisfactory high value for the tablet porosities have been retained.

The very short disintegration time of 3 min, short hanging tablet slip time of 60 sec and the fast dissolution rate of 90% w/w dissolved after 10 min show that the two formulations have tablet melt characteristics.

Examples 3, 4 Reference Examples 3 and 4

Two reference examples (ref. 3 and 4) based on commercial and granular qualities of calcium carbonate were employed in order to benchmark these formulations against the formulations according to the invention.

| Ingredient (mg) per tablet | Example 3 | Example 4 | Reference example 3 | Reference example 4 |
|---|---|---|---|---|
| Calcium carbonate | 1250 | 1250 | (1250) | (980) |
| Povidone K-30 | 26.3 | 16.4 | | |
| Malic acid | | 4.2 | | |
| Sucralose | 0.50 | 0.50 | 0.5 | 0.30 |
| Xylitol (gran. liquid) | 56.6 | 66.5 | | |
| % binder* in gran. liq. | 15.8 | 10 | | |
| % filler** in gran. liq. | 34 | 40 | | |
| Wht. Gran. liq. | 400 | 400 | | |
| Xylitol (dry mixture) | 66.6 | 66.6 | 11.5 | |
| Lycatab Mineral CC 190 | | | 1388 | |
| Formaxx $CaCO_3$ 70 | | | | 1399.7 |
| Dried granulate | 1400 | 1400 | | |
| Durarome lemon | 14 | 14 | 14 | 14 |
| Mg. stearate | 6 | 6 | 6 | 6 |
| Tablet weight | 1420 | 1420 | 1420 | 1420 |
| Characterization of Granulate: | | | | |
| Bulk density | | | | |
| Mavern $D_{10}$ (µm) | 43 | 67 | 100 | 141 |
| Malvern $D_{50}$ (µm) | 167 | 150 | 176 | 220 |
| Malvern $D_{90}$ (µm) | 348 | 276 | 300 | 341 |
| Span value | 1.83 | 1.39 | 1.14 | 0.91 |
| Characterization of tablet: | | | | |
| Tabletting pressure (kN) | 10 | 9 | 14 | 6 |
| Tablet density (g/cm³) | 1.71 | 1.54 | 1.71 | 1.43 |
| Tablet porosity (%) | 30.4 | 37.4 | 32.5 | 33.1 |
| Crushing strength (N) | 44 | 46 | 44 | 45 |
| Friability (%) | 0.5 | 1.2 | 1.7 | 1.9 |
| Disintegration | 135 sec | 70 sec | >30 min | >30 min |
| Hanging tablet slip time (sec) | 38 | 24 | 13 min | >30 min |
| Dissol. rate, 10 min (%) | 91 | 90 | 17 | 42 |

*the term "binder" used in connection with the granulation liquid (or film-coating composition) is equivalent with the term "polymeric substance"
**the term "filler" used in connection with the granulation liquid (or film-coating composition) is equivalent with the term "water-soluble substance"

Example 3 and 4 according to the invention and reference example 3 and 4 have been made with the same amount of flavoring, intense sweetener and tablet lubricant in order to compare these with respect to tablet characteristics and sensory properties.

Example 3 and 4 according to the invention are characterized as being dense tablets with apparent tablet densities in the range of 1.5 to 1.7 g/cm³, which facilitates the formulation of small tablets. The tablets are also characterized by a sufficient high value for the porosity, which is in the range of 30 to 38%. It can also be seen that example 3 and 4 produces tablets with a satisfactory crushing strength and friability of 40-50 N and 0.5 to 1.2%, respectively, at low tabletting pressures of 9 to 10 kN. The tablets are further characterized with a fast disintegration time of 1-3 min and a quick dissolution rate where 90% w/w is dissolved after 10 min. The hanging tablet slip time for example 4 is only 24 sec, which gives evidence of the excellent melt properties of this formulation.

Reference example 3 is a tablet based on Lycatab Mineral CC 190 from Roquette Freres. This quality is based on a Scoralite quality from Score Watrigant SA, France that has been granulated with 10% maize starch.

This quality produces dense tablets but the disintegration time is above 30 min and dissolution of calcium is only 17% w/w after 10 min, which does not satisfy the in vitro requirements for a melt tablet containing calcium.

Reference example 4 is a tablet based on Formaxx $CaCO_3$ from Merck Kg A, Germany consisting of 70% of calcium carbonate, which has been produced by a spraydrying process. Only 980 mg calcium carbonate could be incorporated into this tablet in order to achieve a tablet weight of 1420 mg as this granulate only contains 70% calcium carbonate. It is also a less dense tablet due to the high porosity of the spray-dried material. Reference example 4 exhibit inferior properties with respect to disintegration and dissolution rate when compared to examples according to the invention. Both of the reference examples have high values for the hanging tablet slip time, which indicates that the formulations do not have melt properties.

Figure 5:
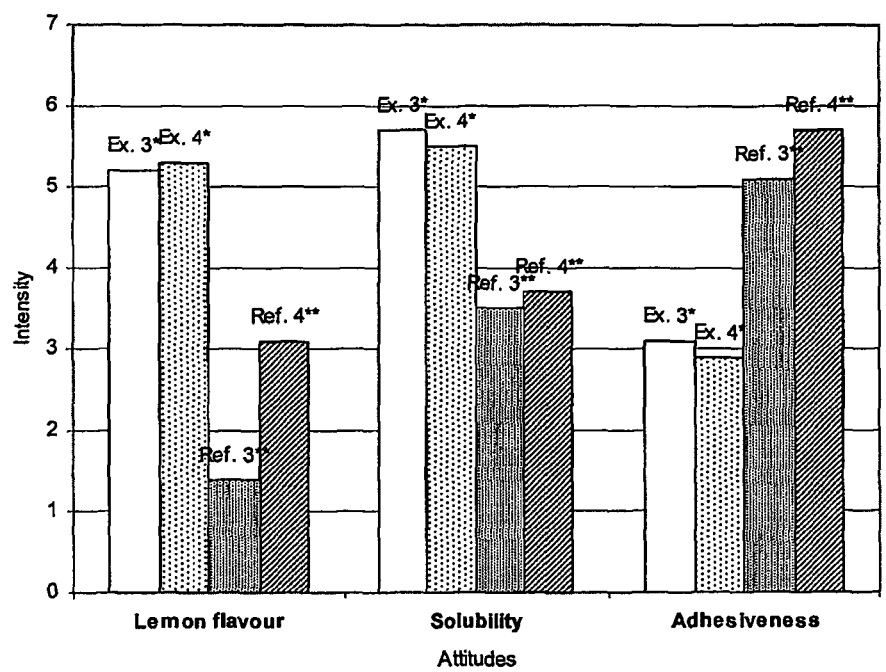
FIG. 5 shows the results from the sensory analysis of examples 3 and 4.

The four formulations were compared with each other by a sensory analysis as described under the detailed description of the invention. The four formulations contained the same amount and type of flavour, intense sweetener and tablet lubricant except for the sweetener level in example 4 due to the higher content of sorbitol in this formulation. FIG. 5 visualize the results of a sensory analysis carried out with the four formulations.

Examples 3 and 4 are marked with one asterix in FIG. 5 where both examples are statistically different on all three attitudes at a 95% confidence level from the two reference examples marked with two asterixes.

Examples 3 and 4 according to the invention came out best with respect to lemon flavor although the four formulations contained the same amount of flavor. The reason for this is due to the improved disintegration/dispersion and flavor release in the mouth for example 3 and 4.

Examples 3 and 4 according to the invention were tested against a reference based on a calcium chewable tablet according to European application EP-A-1128815 of Nycomed Pharma. Both of the formulations according to the invention came out with a significantly shorter met dispersion time when compared against the reference tablet.

of 3.8, 9.8, 15.8, 21.8 and 27.9% w/w to the granulation liquid where the amount of xylitol was adjusted in order to have a constant dry matter content of 50% w/w in the granulation liquid.

| Ingredient (mg) per tablet | Example 5 | Example 6 | Example 7 | Example 8 | Example 9 |
|---|---|---|---|---|---|
| Calcium carbonate | 1250 | 1250 | 1250 | 1250 | 1250 |
| Povidone K-30 | 6.4 | 16.4 | 26.3 | 36.4 | 46.5 |
| Malic acid | | | | | |
| Sucralose | 0.50 | 0.50 | 0.50 | 0.50 | 0.50 |
| Xylitol (gran. liquid) | 76.5 | 66.5 | 56.6 | 46.5 | 36.4 |
| % binder* in gran. liq. | 3.8% | 9.8% | 15.8% | 17% | 28% |
| % filler** in gran. liq. | 45.9% | 40% | 34% | 33% | 22% |
| Wht. Gran. liq. | 400 | 400 | 400 | 400 | 400 |
| Xylitol (dry mixture) | 66.6 | 66.6 | 66.6 | 66.6 | 66.6 |
| Lycatab Mineral CC 190 | | | | | |
| Formaxx $CaCO_3$ 70 | | | | | |
| Dried granulate | 1400 | 1400 | 1400 | 1400 | 1400 |
| Durarome lemon | 14 | 14 | 14 | 14 | 14 |
| Mg. stearate | 6 | 6 | 6 | 6 | 6 |
| Tablet weight | 1420 | 1420 | 1420 | 1420 | 1420 |
| Characterization of Granulate: | | | | | |
| Bulk density | 0.67 | 0.74 | 0.72 | 0.65 | 0.67 |
| Mavern $D_{10}$ (μm) | 29 | 88 | 65 | 51 | 73 |
| Malvern $D_{50}$ (μm) | 95 | 167 | 166 | 180 | 220 |
| Malvern $D_{90}$ (μm) | 228 | 345 | 319 | 397 | 471 |
| Span value | 2.10 | 1.31 | 1.53 | 1.93 | 1.81 |
| Characterization of tablet: | | | | | |
| Tabletting pressure (kN) | 18 | 14 | 10 | 10 | 8 |
| Tablet density (g/cm³) | 1.68 | 1.61 | 1.67 | 1.60 | 1.59 |
| Tablet porosity (%) | 31.9 | 34.9 | 32.1 | 34.9 | 35.1 |
| Crushing strength (N) | 42 | 47 | 58 | 73 | 69 |
| Friability (%) | 2.2 | 1.7 | 0.8 | 0.8 | 0.3 |
| Disintegration (sec) | 99 | 82 | 95 | 152 | 148 |
| Hanging tablet slip time (sec) | 29 | 23 | 29 | 44 | 48 |

*the term "binder" used in connection with the granulation liquid (or film-coating composition) is equivalent with the term "polymeric substance"
**the term "filler" used in connection with the granulation liquid (or film-coating composition) is equivalent with the term "water-soluble substance)

Example 4 had the best melt characteristics with a melt dispersion time of 52 seconds. There was also a statistically difference between examples 3 and 4 with respect to the melt dispersion time. The results have been depicted in FIG. 6.

Thus it has been shown that compositions according to the invention has got superior tablet characteristics and improved sensory properties comparing to commercial calcium carbonate qualities, which have been recommended for use in chewable tablets. It has furthermore been shown that the calcium melt formulations according to the invention have a significantly shorter melt dispersion time when compared to a calcium tablet based on European application EP-A-1128815 of Nycomed Pharma. These superior properties have been accomplished in spite of the fact that the tablets are dense and thus also offer reduced tablet volumes and tablet sizes/diameters.

Examples 6, 7, 8 and 9

A series of examples were carried out in order to vary the proportion between the polymeric substance (also denoted binder material) and the water-soluble substance (also denoted soluble filer). The polymeric binder material, which in this case was Povidone K-30, was added in concentrations The mean particle size can be seen to increase as the binder concentration in the granulate increases. The granulates are further characterized by low values for the span values which indicate narrow particle she distributions. From the table it can be seen that as little as 0.5% of povidone K-30 per tablet weight produces tablets with an acceptable crushing strength and friability. The crushing strength is increased and the friability values decreased as the binder concentration in the granulates increases.

It can also bee seen that the disintegration and the hanging tablet slip time increase as the binder content in the tablet increases. This is due to the presence of a more viscous film around the calcium carbonate crystals, which reduces the water ingress to a slight extent. The best melt properties for the above series of examples are seen with binder (povidone K-30) contents of 6 to 26 mg, which is equivalent to 0.4 to 1.8% w/w of binder in the tablet formulations.

Examples 10, 11, 12, 13, 14 and 15

The flexibility of the type of filler material in the coating of the calcium carbonate crystals has been investigated in the below examples.

| Ingredient (mg) per tablet | Ex. 10 | Ex. 11 | Ex. 12 | Ex. 13 | Ex. 14 | Ex. 15 |
|---|---|---|---|---|---|---|
| Calcium carbonate | 1250 | 1250 | 1250 | 1250 | 1250 | 1250 |
| Povidone K-30 | 26.3 | 26.3 | 36 |  | 26 | 26 |
| Copovidone |  |  |  | 46.7 |  |  |
| Malic acid |  |  |  |  |  |  |
| Sucralose | 0.5 | 0.5 | 0.5 | 0.5 | 0.5 | 0.5 |
| sorbitol (gran. liquid) | 56.6 |  |  |  |  |  |
| Maltitol (gran. liquid) |  | 56.6 |  |  |  |  |
| Mannitol (gran. liquid) |  |  | 25 |  |  |  |
| Isomalt (gran. liquid) |  |  |  | 33.3 |  |  |
| Lactitol (gran. liq.) |  |  |  |  | 57 |  |
| Dextrose anhyd. (gran. liq.) |  |  |  |  |  | 56.8 |
| % age binder in gran. liq. | 15.8 | 15.8 | 21.6 | 28 | 15.6 | 15.6 |
| % age filler in gran. liq. | 34 | 34 | 15 | 20 | 34.2 | 34.1 |
| Wht. Gran. liq. | 400 | 400 | 400 | 400 | 400 | 400 |
| Xylitol (dry mixture) | 66.6 | 66.6 | 66.7 | 66.5 | 66.5 | 66.7 |
| Dried granulate | 1400 | 1400 | 1400 | 1397 | 1400 | 1400 |
| Durarome lemon | 14 | 14 | 14 |  | 14 | 14 |
| Flavour granulate |  |  |  | 42 |  |  |
| Mg. stearate | 6 | 6 | 6 | 5 | 5 | 5 |
| Tablet weight | 1420 | 1420 | 1420 | 1444 | 1419 | 1419 |
| Characterization of Granulate: |  |  |  |  |  |  |
| Bulk density | 0.61 | 0.65 | 0.69 | 0.73 | 0.77 | 0.78 |
| Mavern $D_{10}$ (μm) | 70 | 79 | 97 | 63 | 154 | 132 |
| Malvern $D_{50}$ (μm) | 199 | 222 | 230 | 256 | 307 | 268 |
| Malvern $D_{90}$ (μm) | 372 | 433 | 448 | 598 | 559 | 493 |
| Span value | 1.52 | 1.60 | 1.53 | 2.09 | 1.32 | 1.35 |
| Characterization of tablet: |  |  |  |  |  |  |
| Tabletting pressure (kN) | 8 | 10 | 10 | 14 | 10 | 10 |
| Tablet density (g/cm$^3$) | 1.57 | 1.61 | 1.61 | 1.63 | 1.66 | 1.65 |
| Tablet porosity (%) | 36.0 | 34.0 | 34.3 | 32.5 | 32.0 | 32.8 |
| Crushing strength (N) | 71 | 117 | 79 | 41 | 112 | 94 |
| Friability (%) | 0.4 | 0.1 | 0.4 |  | 0.1 | 0.1 |
| Disintegration (sec) | 179 | 123 | 125 | 161 | 124 | 125 |
| Hanging tablet slip time (sec) | 71 | 81 | 66 | 159 | 201 | 78 |

\* the term "binder" used in connection with the granulation liquid (or film-coating composition) is equivalent with the term "polymeric substance"
\*\* the term "filler" used in connection with the granulation liquid (or film-coating composition) is equivalent with the term "water-soluble substance)

From the results it can be seen that a number of filler materials can be employed as a component in the coating of the calcium carbonate crystals. Satisfactory agglomeration it achieved with mean particle sizes in the range of 200 to 307 μm and with low span values indicating narrow particle size distributions.

It can be seen that the formulations produce dense tablets in the range of 1.57 to 1.66 g/cm$^3$ and with sufficiently high values for the porosity in the range of 32 to 36%. The values for the disintegration time and hanging tablet slip time are slightly higher than those achieved for xylitol which indicate that xylitol is one of the preferred filler materials in the film covering the calcium carbonate crystals.

Relatively high crushing strengths of 70 to 117 N and very low friability values of 0.1 to 0.4% are achieved at low tabletting pressures of 8 to 10 kN.

Examples 16, 17, 18 And 19

Different qualities of calcium carbonate and different types of wet binder material in the coating of the calcium carbonate crystals has been investigated n the below examples.

| Ingredient (mg) per tablet | Ex. 16 | Ex. 17 | Ex. 18 | Ex. 19 |
|---|---|---|---|---|
| Calcium carbonate | 1250 | 1250 |  |  |
| Sturcal M (CaCO$_3$) |  |  | 1250 |  |
| Hubercal 500 Elite (CaCO$_3$) |  |  |  | 1250 |
| Povidone K-30 |  |  | 26 | 26 |
| Inulin | 25 |  |  |  |
| Propylene glycol alginate |  | 1.33 |  |  |
| Sucralose | 0.5 | 0.5 | 0.5 | 0.5 |
| Xylitol (gran. liquid) | 55 |  | 57 | 57 |
| Sorbitol (gran. liquid) |  | 81.5 |  |  |
| % age binder in gran. liq. | 15 | 0.8 | 15.6 | 15.6 |
| % age filler in gran. liq. | 33 | 48.9 | 34.2 | 34.2 |
| Wht. Gran. liq. | 400 | 400 | 400 | 400 |
| Xylitol (dry mixture) | 44.5 | 66.7 | 66.5 | 66.5 |
| Dried granulate | 1375 | 1400 | 1400 | 1400 |
| Durarome lemon |  | 14 | 14 | 14 |
| Flavour granulate | 41 |  |  |  |
| Mg. stearate | 5 | 5 | 5 | 5 |
| Tablet weight | 1421 | 1419 | 1419 | 1419 |
| Characterization of Granulate: |  |  |  |  |
| Bulk density | 0.71 | 0.81 | 0.63 | 0.75 |
| Mavern $D_{10}$ (μm) | 37 | 116 | 23 | 48 |
| Malvern $D_{50}$ (μm) | 100 | 266 | 273 | 212 |
| Malvern $D_{90}$ (μm) | 253 | 601 | 548 | 455 |

-continued

| Ingredient (mg) per tablet | Ex. 16 | Ex. 17 | Ex. 18 | Ex. 19 |
|---|---|---|---|---|
| Span value | 2.16 | 1.81 | 1.92 | 1.91 |
| Characterization of tablet: | | | | |
| Tabletting pressure (kN) | 14 | 10 | 8 | 8 |
| Tablet density (g/cm$^3$) | 1.66 | 1.73 | 1.38 | 1.52 |
| Tablet porosity (%) | 32.6 | 29.6 | 41.3 | 38.1 |
| Crushing strength (N) | 43 | 94 | 80 | 51 |
| Friability (%) | 1.4 | 0.1 | 1.2 | 1.5 |
| Disintegration (sec) | 50 | 155 | 196 | 389 |
| Hanging tablet slip time (sec) | 23 | 326 | 56 | 166 |

*the term "binder" used in connection with the granulation liquid (or film-coating composition) is equivalent with the term "polymeric substance"
**the term "filler" used in connection with the granulation liquid (or film-coating composition) is equivalent with the term "water-soluble substance)

From the results it can be seen that different binder materials can be employed as a component in the coating of the calcium carbonate crystals.

Example 17 contains propylene glycol alginate, which is only present in a concentration of 0.09% in the tablet. It is however a very viscous binder in low concentrations, which explains the high value for the hanging tablet slip time.

Example 18 and 19 show that different qualities of calcium carbonate with specific surface area up to 1.5 m$^2$/g can be used with good results with respect to granulate and tablet characteristics.

Examples 20, 21, 22, 23 and 24

A series of examples were carried out in order to vary the amount of water-soluble substance (also denoted soluble filer). The soluble filer was added in amounts of 4.2, 2.2 1.1 and 0.6% w/w to the tablet where the amount of polymeric binder was kept at two levels of 16 and 26 mg per tablet respectively.

| Ingredient (mg) per tablet | Composition | | | | |
|---|---|---|---|---|---|
| | Ex. 20 | Ex. 21 | Ex. 22 | Ex. 23 | Ex. 24 |
| Calcium carbonate | 1250 | 1250 | 1250 | 1250 | 1250 |
| Povidone K-30 | 16 | 16 | 26 | 26 | 26 |
| Sucralose | 0.5 | 0.5 | 0.5 | 0.5 | 0.5 |
| Xylitol (gran. liquid) | 56.5 | 28.5 | 28.5 | 14.5 | 7.5 |
| % binder* in gran. liq. | 11.0 | 17.8 | 16.5 | 22.2 | 26.8 |
| % filler** in gran. liq. | 38.7 | 31.7 | 18.1 | 12.4 | 7.7 |
| Wht. Gran. liq. | 350 | 225 | 393 | 293 | 243 |
| Dried granulate | 1323 | 1295 | 1305 | 1291 | 1284 |
| Durarome lemon | 13 | 13 | 13 | 13 | 13 |
| Mg. stearate | 4 | 4 | 4 | 4 | 4 |
| Tablet weight | 1340 | 1312 | 1322 | 1308 | 1301 |
| Characterization of Granulate: | | | | | |
| Bulk density (g/ml) | 0.69 | 0.66 | 0.61 | 0.61 | 0.70 |
| Mavern D$_{10}$ (μm) | 43 | 29 | 59 | 34 | 23 |
| Malvern D$_{50}$ (μm) | 130 | 110 | 135 | 121 | 92 |
| Malvern D$_{90}$ (μm) | 262 | 261 | 248 | 266 | 249 |
| Span value | 1.68 | 2.11 | 1.40 | 1.92 | 2.46 |
| Characterization of tablet: | | | | | |
| Tabletting pressure (kN) | 20 | 35 | 25 | 25 | 46 |
| Tablet density (g/cm$^3$) | 1.70 | 1.80 | 1.74 | 1.73 | 1.82 |
| Tablet porosity (%) | 33.2 | 31.0 | 32.1 | 33.3 | 30.1 |

-continued

| Ingredient (mg) per tablet | Composition | | | | |
|---|---|---|---|---|---|
| | Ex. 20 | Ex. 21 | Ex. 22 | Ex. 23 | Ex. 24 |
| Crushing strength (N) | 34 | 35 | 33 | 39 | 45 |
| Friability (%) | 2.0 | 0.9 | 0.2 | 0.6 | 1.1 |
| Disintegration (sec) | 57 | 69 | 101 | 89 | 123 |
| Hanging tablet slip time (sec) | 25 | 40 | 45 | 50 | 65 |

*the term "binder" used in connection with the granulation liquid (or film-coating composition) is equivalent with the term "polymeric substance"
**the term "filler" used in connection with the granulation liquid (or film-coating composition) is equivalent with the term "water-soluble substance)

The granulates are further characterized by low values for the span values which indicate narrow particle size distributions. From the table it can be seen that as little as 7.5 mg or 0.6% of xylitol per tablet produces tablets with an acceptable crushing strength and friability. It can further be seen that the tablet formulations are characterised by high tablet densities due to the low levels of soluble filler material in the tablets. Accordingly, use of a combination of a water-soluble substance and a polymeric substance to coat or partly coat a calcium-containing compound enables preparation of tablets with a surprisingly high content of the Ca-compound. In the present example, the tablet is designed as a chewable tablet, but it has characteristics that also enable normal oral administration, i.e. by swallowing the tablet. In such a case, the Ca-content will be even higher (97% w/w) due to the fact that for swallowable tablets flavor can be omitted.

Tablet melt characteristics are achieved for the whole series of formulations with disintegration time and hanging tablet slip time in the range of 57-123 sec and 25-65 sec respectively.

It is surprising that tablet melt function characteristics is retained at these low excipient levels where the active ingredient is present in an amount exceeding 96% (ex. 24).

Examples 25, 26 and 27

A series of examples were carried out in order to use other calcium salts and especially calcium salts based on organic acids. Combinations of calcium carbonate with calcium lactate and calcium citrate have also been formulated in order to have a sufficient amount of calcium in each tablet. Ex. 25, 26 and 27 contain 350, 400 and 200 mg respectively of calcium per tablet.

| Ingredient (mg) per tablet | Composition | | |
|---|---|---|---|
| | Ex. 25 | Ex. 26 | Ex. 27 |
| Calcium carbonate | 700 | 800 | |
| Calcium lactate (13.7%) | 509 | | 290 |
| Calcium citrate (21.0%) | | 381 | 761 |
| Povidone K-30 | 11.2 | 12.8 | 12.8 |
| Sucralose | 0.35 | 0.4 | 0.4 |
| Xylitol (gran. liquid) | 93.7 | 106.8 | 112.8 |
| % binder* in gran. liq. | 6.4 | 6.4 | |
| % filler** in gran. liq. | 53.4 | 53.4 | |
| Dried granulate (m | 1317 | 1301 | 1177 |

-continued

| Ingredient (mg) per tablet | Composition | | |
|---|---|---|---|
| | Ex. 25 | Ex. 26 | Ex. 27 |
| Durarome lemon | 13 | 13 | 13 |
| Mg. stearate | 4 | 5 | 4 |
| Tablet weight | 1334 | 1319 | 1194 |
| Characterization of Granulate: | | | |
| Bulk density (g/ml) | 0.58 | 0.75 | 0.72 |
| Mavern $D_{10}$ (μm) | 116 | 41 | 49 |
| Malvern $D_{50}$ (μm) | 231 | 100 | 97 |
| Malvern $D_{90}$ (μm) | 418 | 227 | 279 |
| Span value | 1.31 | 1.86 | 2.37 |
| Characterization of tablet: | | | |
| Tabletting pressure (kN) | 10 | 24 | 14 |
| Tablet density (g/cm$^3$) | 1.26 | 1.52 | 1.03 |
| Tablet porosity (%) | 35.1 | 32.0 | 39.0 |
| Crushing strength (N) | 44 | 37 | 44 |
| Friability (%) | 1.7 | 1.6 | 1.7 |
| Disintegration (sec) | 92 | 78 | 50 |
| Hanging tablet slip time (sec) | 90 | 35 | 95 |

*the term "binder" used in connection with the granulation liquid (or film-coating composition) is equivalent with the term "polymeric substance"
**the term "filler" used in connection with the granulation liquid (or film-coating composition) is equivalent with the term "water-soluble substance)

It is seen from the above table that tablet melt tablets are achieved with acceptable friabilities and crushing strengths at low tabletting pressures. Tablet melt characteristic are evident with disintegration and hanging tablet slip times of 50-92 sec and 35-95 sec respectively.

The tablet density can be seen to be dependent on the particular calcium salt or combination of calcium salts used where tablets based on organic calcium salts are less dense than tablets based mainly on calcium carbonate.

Example 28

Wet Granulation in a High Shear Mixer
28A. Design
Compositions to be tested in this experiment are as follows

| Raw materials | Amounts in percent |
|---|---|
| Calcium carbonate | 50-95 |
| Water-soluble substance | 3-40 |
| Polymeric substance with binding properties | 0.5-5 |
| Flavor | 0.1-5 |
| Vitamin $D_3$ powder | 0.1-5.5 |
| Magnesium stearate | 0.2-2 |

Calcium carbonate is mixed with a part of the soluble filler.

The mixture is wetted with a solution/suspension of the rest of the water-soluble substance and the polymeric substance with binding properties, the solution/suspension is sprayed on to the powder mixture by use of a nozzle. The objective of the spraying is to obtain substantially film-coated calcium carbonate particles and/or crystals.

The wetted powder mass is wet massed between 1 and 10 minutes.

The granulated powder mass is transferred to a fluid bed dryer where it is dried to a water content below 1.0%.

The dried granulate is passed through a 1.5 mm screen and mixed with the remaining excipients to the final granulate.

The final granulate is compressed to chewable tablets.
28B. Plot Scale Experiment One example has been carried out in a pilot scale high speed mixer in order to show that other granulation processes may be used to produce tablet melt formulations according to the invention.

The granulation was carried out in a Fielder PMA 25 with a batch size of 6 kg. The main impeller and the knife were set to mixing speeds of 400 RPM and 3000 RPM respectively. 300 g of granulation liquid with a dry matter content of 60% was applied to the powder mixture with a spray rate of 80 g/min and at a spray atomization pressure of 1.5 bar.

The wet granulated product was subsequent passed through a 12 mesh screen and 3 kg transferred to a plot scale fluid bed (Glatt GPCG 3) for drying.

The product was dried at 80° C. until an end moisture content of 0.1%. The dried granulate was then mixed with flavour granulate and magnesium stearate and 14 mm normal convex tablets were produced.

| Ingredient (mg) per tablet | Composition Ex. 28 |
|---|---|
| Calcium carbonate | 1250 |
| Povidone K-30 | 16 |
| Sucralose | 0.5 |
| Xylitol | 133.5 |
| % binder* in gran. liq. | 6.4 |
| % filler** in gran. liq. | 53.4 |
| Dried granulate | 1400 |
| Durarome lemon | 14 |
| Mg. stearate | 5 |
| Tablet weight | 1419 |
| Characterization of Granulate: | |
| Bulk density (g/ml) | 0.76 |
| Mavern $D_{10}$ (μm) | 30 |
| Malvern $D_{50}$ (μm) | 63 |
| Malvern $D_{90}$ (μm) | 614 |
| Span value | |
| Characterization of tablet: | |
| Tabletting pressure (kN) | 38 |
| Tablet density (g/cm$^3$) | 1.72 |
| Tablet porosity (%) | 30.1 |
| Crushing strength (N) | 41 |
| Friability (%) | 1.5 |
| Disintegration (sec) | 83 |
| Hanging tablet slip time (sec) | 50 |

*the term "binder" used in connection with the granulation liquid (or film-coating composition) is equivalent with the term "polymeric substance"
**the term "filler" used in connection with the granulation liquid (or film-coating composition) is equivalent with the term "water-soluble substance)

The above example shows that calcium melt tablets can be used with granulation technologies other than fluid bed. Calcium melt tablets have been achieved with a low value for the friability and acceptable crushing strength at a tabletting pressure of 38 kN. Tablet melt characteristics were evident with a disintegration time of 83 sec and a hanging tablet slip time of 50 sec.

The tablet formulation based on high shear granulation has a high density of 1.72 g/cm$^3$ and a porosity of 30.1%. The density is higher and the porosity somewhat lower compared to the formulations based on fluid bed granulation/coating in this invention. This is expected due to the fact that a high shear mixer produces a more dense granulate during the wet massing at high shear rates in the mixer.

Example 29

Production Scale Manufacture of Calcium Carbonate Containing Granulate

Granulates having a composition per unit dose within the following intervals were manufactured:

| Raw material | Lower limit [unit dose] | Upper limit [unit dose] |
|---|---|---|
| Calcium carbonate | 250 mg | 1000 mg |
| Xylitol | 5 mg | 800 mg |
| Povidone 30 | 2 mg | 80 mg |
| Artificial sweetener | 0.1 mg | 20 mg |

The granulation trials were performed in a Glatt fluid bed granulator using a multiple headed nozzle (2.3 mm). The batch size was 250 kg.

Calcium carbonate was transferred to product container and xylitol, povidone 30 and artificial sweetener were dissolved in the water.

The powder bed was heated to a temperature of 35-40° C. before starting the granulation. Inlet air temperature was kept at 80° C. during the entire test until the cooling step. Product temperature was kept at 35-40° C. during the granulation step where an atomizing air pressure of approximately 4.5 bar was used to atomize the granulation liquid. During drying the product temperature was raised to 50-52° C. where after the inlet air temperature was lowered to 20° C. starting the cooing step. Reaching a product temperature of 40-45° C. the cooling was stopped and the granulate was discharged from the fluid bed.

6 trials were performed. Trial 1-4 were set up in a $2^2$ factorial design where xylitol/povidone 30 level and spray rate (granulation liquid) were the independent variables. In trial 5 the level of xylitol was increased and the level of povidone 30 was decreased compared to the factorial design. In trial 6 the level of xylitol was decreased and the level of povidone 30 was increased compared to the factorial design.

Composition of Trial 1-6 in mg/tablet

| Raw material | Trial 1 | Trial 2 | Trial 3 | Trial 4 | Trial 5 | Trial 6 |
|---|---|---|---|---|---|---|
| Calcium carbonate | 1250.0 | 1250.0 | 1250.0 | 1250.0 | 1250.0 | 1250.0 |
| Xylitol | 133.5 | 133.5 | 170.5 | 170.5 | 170.5 | 83.5 |
| Povidone 30 | 16.0 | 16.0 | 16.0 | 16.0 | 12.0 | 26.0 |
| Sucralose | 0.5 | 0.5 | 0.5 | 0.5 | 0.5 | 0.5 |
| Spray time [min] | 41.4 | 25 | 55 | 31 | 30 | 23 |

In order to determine the degree of coverage (coating) of the calcium carbonate crystals, by the solids in the granulation liquid, in the manufactured granulate XPS (X-ray Photoelectron Spectroscopy) measurements were made on Trial 1, 2 and 4.

Results showing that the surface of the granulates is covered are given below:

Percentage of the granule surface coated by:

| | [Percent coverage] | | |
|---|---|---|---|
| Material | Test 1 | Test 2 | Test 4 |
| Calcium carbonate (not coated) | 23.9 | 26.9 | 20.9 |
| Povidone 30 | 48.6 | 44.1 | 45.4 |
| Xylitol | 26.0 | 28.0 | 32.2 |
| Sucralose | 1.5 | 1.0 | 1.5 |

It is observed that even a long granulation time, which should result in a more homogeneous distribution, does not ensure a complete coverage of the calcium carbonate crystals by the binder (Povidone 30) and water soluble filler (xyitol).

Particle size distribution of the granulates are measured by laser diffraction (Malvern) [µm]:

| Trial no. | $D_{10}$ | $D_{50}$ | $D_{90}$ |
|---|---|---|---|
| Trial 1 | 44 | 149 | 304 |
| Trial 2 | 74 | 171 | 351 |
| Trial 3 | 51 | 137 | 268 |
| Trial 4 | 75 | 165 | 373 |
| Trial 5 | 71 | 163 | 398 |
| Trial 6 | 69 | 175 | 394 |

Bulk density of the granulates [g/ml]:

| | Trial no: | | | | | |
|---|---|---|---|---|---|---|
| | Trial 1 | Trial 2 | Trial 3 | Trial 4 | Trial 5 | Trial 6 |
| Bulk density | 0.79 | 0.82 | 0.80 | 0.85 | 0.86 | — |

A statistical analysis of the trials which are part of the factorial design shows a significant statistical effect for spray rate. An increase in spray rate results in an increase in $D_{50}$ and $D_{10}$.

The analysis also shows a significant statistical effect for low amounts of xylitol resulting in increasing bulk densities. This is also valid for the combination of low amounts of xylitol and high spray rates.

Example 30

Manufacture of Calcium Carbonate Containing Tablets

Final granulates were prepared by admixing Durarome® flavour granulate and magnesium stearate to the granulates obtained in Example 29 and extra-granule excipients were added.

| | Test 1 and 2 | Test 3 and 4 | Test 5 | Test 6 |
|---|---|---|---|---|
| Granulate | 1400 mg | 1437 mg | 1433 mg | 1360 mg |
| Flavour granulate | 14 mg | 14 mg | 14 mg | 14 mg |
| Magnesium stearate | 5 mg | 5 mg | 5 mg | 5 mg |
| Tablet weight | 1419 mg | 1456 mg | 1452 mg | 1379 mg |

Tablets were manufactured from the final granulates.

The tablets were compressed on a 16 station B3B (Manesty) using 14 mm normal concave punches and the following compression forces: 0.6 ton, 1.0 ton, 1.4 ton, 1.8 ton and 2.2 ton. Crushing strength-compression force profiles were obtained; see FIG. 8, as well as disintegration time, tablet porosity (1 ton compression force).
Tablet Technical Data (1 Ton Compression Force):

| Trial no: | Disintegration time [sec] | Tablet porosity [%] |
|---|---|---|
| Trial 1 | 68 | 35.2 |
| Trial 2 | 75 | 33.4 |
| Trial 3 | 72 | 32.7 |
| Trial 4 | 69 | 36.1 |
| Trial 5 | 50 | 37.6 |
| Trial 6 | 68 | 39.5 |

The statistical analysis of batch 1-4 which go in to a $2^2$ factorial design shows no significant effects, which is pointing towards a very robust tableting process.

Figure 8:
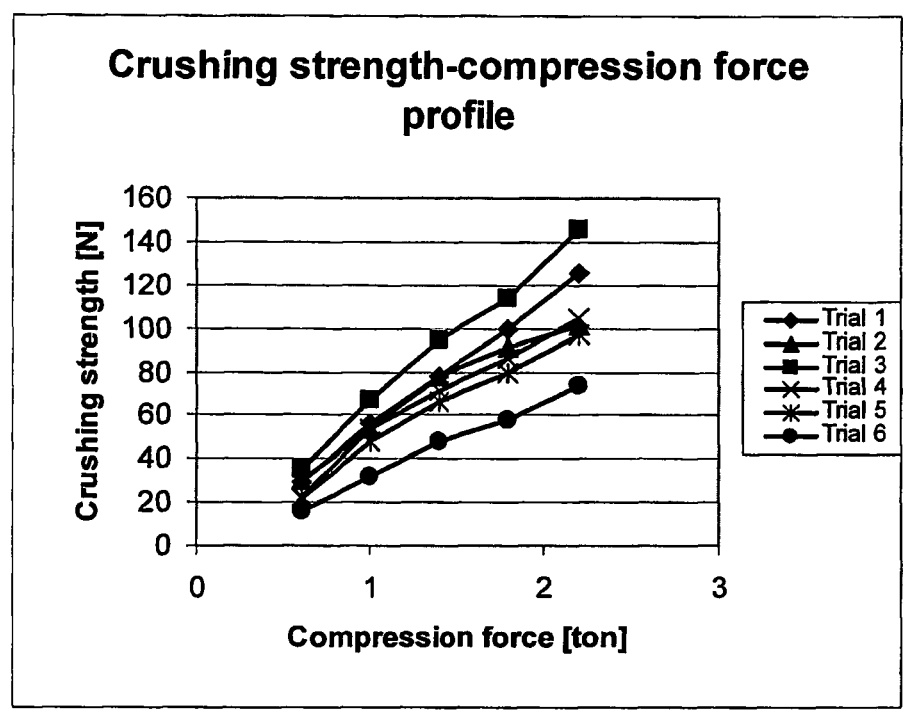
FIG. 8 illustrates crushing strength-compression force profiles.

This is also illustrated by the tablet technical data and the crushing strength-compression force profiles in FIG. 8.

Trial 5 and 6 are not part of the factorial design, however, from a practical point of view neither disintegration time or tablet porosity for this two trials deviates significantly from the results in the design.

From FIG. 8 it is seen that the crushing strength level of trial 6 is lower than the slopes for the rest of the trials. This is probably caused by the lower amount of xylitol in that formulation (see Example 29).

Example 31

Test of Alternative Polymeric Compounds

Agar and Kollicoat IR in different concentrations were tested according to the following design:
Granulat Composition (Per Batch):

|  | Low Agar | Medium Agar | High Agar | Low Kollicoat | Medium Kollicoat | High Kollicoat |
|---|---|---|---|---|---|---|
| Calcium carbonate Scoralite 1B | 4500 g | 4500 g | 4500 g | 4500 g | 4500 g | 4500 g |
| Xylitol | 408.6 g | 408.6 g | 408.6 g | 408.6 g | 408.6 g | 408.6 g |
| Agar | 42.84 g | 70.56 g | 100.8 g | — | — | — |
| Kollicoat IR | — | — | — | 42.84 g | 70.56 g | 100.8 g |
| Water | 490.0 g | 800.64 g | 1280.60 g | 528.56 g | 541.11 g | 773.1 g |
| Magnesium stearate | 25.2 g | 25.2 g | 25.2 g | 25.2 g | 25.2 g | 25.2 g |
| Tablet weight | 1382.4 mg | 1390.1 mg | 1398.5 mg | 1382.4 | 1390.1 mg | 1398.5 mg |

Calcium carbonate was transferred to the product container in a GPCG 3 fluid bed (Glatt) with a top spray configuration and xylitol and the polymeric compound were dissolved in the water. The calcium carbonate was granulated using the below mentioned process parameters:

| Granulation liquid flow rate: | 120 g/min. |
|---|---|
| Granulation inlet air temperature: | 80° C. |
| Drying inlet temperature: | 80° C. |
| Endpoint temperature drying: | 45° C. |
| Endpoint temperature cooling: | 42° C. |

After cooing the granulates were passed through a 1400 μm screen to remove any over size particles. To obtain the final granulates magnesium stearate was admixed. The granulates were compressed to tablets using 14 mm flat beveled edged punches with a bisect line. Results from the tests can be seen in the result table.

Results

In general it was shown that crushing strength increased for increasing polymeric

| Polymer | Compression force [kN] | Crushing strength [N] | Slip time of hanging tablet [sec.] | Disintegration time [sec.] |
|---|---|---|---|---|
| Agar (low conc.) | 33 | 32 | 37 | 111 |
|  | 46 | 50 | 104 | 154 |
| Agar (medium conc.) | 18 | 19 | 44 | 276 |
|  | 34 | 34 | 69 | 120 |
|  | 46 | 55 | 169 | 292 |
| Agar (high conc.) | 22 | 24 | 83 | 213 |
|  | 33 | 41 | 90 | 82 |
|  | 46 | 64 | 229 | 271 |
| Kollicoat IR (low conc.) | 11 | 25 | 125 | 1415 |
|  | 23 | 52 | 578 | 1800 |
|  | 37 | 80 | 600 | 1800 |
| Kollicoat IR (medium conc.) | 9 | 39 | 105 | 682 |
|  | 20 | 80 | 600 | 962 |
|  | 32 | 109 | 600 | 673 |
| Kollicoat IR (high conc.) | 10 | 53 | 600 | 1504 |
|  | 20 | 103 | 600 | 1425 |
|  | 27 | 126 | 600 | 1415 | concentration as it also was the case for slip time for hanging tablets. As it also can be seen from result table it is necessary to carefully select process- and formulation parameters in order to achieve satisfactory products.

Example 32

Test of Alternative Soluble Compounds

Citric acid, glycin, sodium chloride and sodium ascorbate were tested according to the following design:
Granulat Composition (Per Batch):

|  | Citric acid | Glycin | Sodium chloride | Sodium ascorbate |
|---|---|---|---|---|
| Calcium carbonate Scoralite 1B | 4500 g | 4270 g | 4500 g | 4500 g |
| Citric acid monohydrate | 439.9 g | — | — | — |
| Glycin | — | 381.1 g | — | — |
| Sodium chloride | — | — | 386.4 g | 396.1 g |
| Sodium ascorbate | — | — | — | — |
| Povidone 30 | 56.99 g | 54.74 g | 54.5 g | 55.8 g |
| Water | 439.6 g | 2042.3 g | 1159.1 g | 792.3 |

Calcium carbonate was transferred to the product container in a GPCG 3 fluid bed (Glatt) with a top spray configuration and the soluble compound and Povidone 30 were dissolved in the water. The calcium carbonate was granulated using the below mentioned process parameters:

| | |
|---|---|
| Granulation liquid flow rate: | 120 g/min. |
| Granulation inlet air temperature: | 80° C. |
| Drying inlet temperature: | 80° C. |
| Endpoint temperature drying: | 45° C. |
| Endpoint temperature cooling: | 42° C. |

After cooling the granulates were passed through a 1400 µm screen to remove any over size particles. Final granulates were obtained by admixing magnesium stearate to the screened granulates:

Final Granulate Composition (Per Batch):

| | Citric acid | Glycin | Sodium chloride | Sodium ascorbate |
|---|---|---|---|---|
| Granulate | 3000 g | 3000 g | 3000 g | 3000 g |
| Magnesium stearate | 15.1 g | 15.1 g | 15.1 g | 15.1 g |
| Tablet weight | 1386.5 mg | 1386.5 mg | 1386.5 mg | 1386.5 mg |

From the result table it can be seen that the use of a soluble compound in combination with polymer results in tablets having melt properties.

Results

| Soluble compound | Compression force [kN] | Crushing strength [N] | Slip time of hanging tablet [sec.] | Disintegration time [sec.] |
|---|---|---|---|---|
| Citric acid | 10.0 | 21 | 30 | 46 |
| | 24.6 | 81 | 111 | 122 |
| | 34.4 | 113 | 195 | 181 |
| Glycin | 10.0 | 18 | 26 | 81 |
| | 20.4 | 39 | 49 | 105 |
| | 30.5 | 57 | 94 | 120 |
| Sodium chloride | 10.2 | 17 | 60 | 1086 |
| | 19.6 | 48 | 138 | 1200 |
| | 38.7 | 87 | 300 | 1627 |
| Sodium ascorbate | 17.2 | 44 | 60 | 467 |
| | 25.9 | 68 | 140 | 444 |
| | 38.8 | 96 | 170 | 666 |

In order to achieve satisfactory products it is necessary carefully to select process- and formulation parameters. By combining formulation parameters from Example 31 and 32 it will also be possible to obtain satisfactory products provided suitable process parameters are chosen.

Example 33

Wet Granulation in a Schugi Flexomix System

33A. Design

The compositions to be tested in this experiment are as follows

| Raw materials | Amounts in percent |
|---|---|
| Calcium carbonate | 50-95 |
| Water-soluble substance | 3-40 |
| Polymeric substance with binding properties | 0.5-5 |

-continued

| Raw materials | Amounts in percent |
|---|---|
| Flavor | 0.1-5 |
| Vitamin $D_3$ powder | 0-5.5 |
| Magnesium stearate | 0.2-2 |

Calcium carbonate is mixed with a pert of the soluble filler and passed through the Flexomix-system at a speed between 100 kg/h 5000 kg/h.

The mixture is wetted with a solution/suspension of the rest of the water-soluble substance and the polymeric substance with binding properties; by use of nozzles at a spray rate from 4 kg/h to 700 kg/h. RPM of mixing blades are set between 1000 and 4500.

The granulated powder mass is transferred to a continuous fluid bed dryer where it is dried to a water content below 1.0%.

The dried granulate is passed through a 1.5 mm screen and mixed with the remaining excipients to the final granulate.

The final granulate is compressed to chewable tablets.

33B. Granulation in a Schugi Flexomix, Test of Amount of Soluble Compound, Polymer and Schugi Variables Manufacture of Granulates:

A calcium carbonate powder was transferred to a hopper. A granulation liquid consisting of water and excipients was prepared, see design table for composition, in a jacketed container.

Granulation was performed in a Schugi Flexomix FX-160 with a batch size of approximately 30 kg and a position of the knives of +2. The rotation speed of the mixer shaft was varied between 3500 rpm and 4500 rpm. The feed of the powder was controlled by use of a K-tron T-65 pre-feeder with agitator and a K-tron constant weight feeder WF300. The granulation liquid was added to the powder by atomisation by two nozzles.

The wet granulate was transferred to a horizontal fluid bed dryer and dried to a specified end product temperature.

Design:

| Experiment | (1) | (2) | (3) | (4) | (5) | (6) |
|---|---|---|---|---|---|---|
| Comment | | | | | Replic 4 | Replic 4 |
| Powder mixture: | | | | | | |
| Calcium carbonate % | 100 | 100 | 100 | 100 | 100 | 100 |
| Xylitol % | — | — | — | — | — | — |
| Sorbitol % | — | — | — | — | — | — |
| PVP 30 % | — | — | — | — | — | — |
| Granulation liquid (water) | 39.98 | 38.38 | 38.38 | 38.38 | 38.38 | 38.38 |
| Xylitol % | 53.44 | 57.02 | 57.02 | 57.02 | 57.02 | 57.02 |
| PVP 30 % | 6.38 | 4.39 | 4.39 | 4.39 | 4.39 | 4.39 |
| Sucralose % | 0.20 | 0.22 | 0.22 | 0.22 | 0.22 | 0.22 |
| Schugi rpm | 3500 | 3500 | 4000 | 4000 | 4000 | 4000 |
| Powder flow [kg/h] | 500 | 500 | 500 | 500 | 500 | 500 |
| Granulation liquid flow [kg/h] | 85 | 92 | 78 | 92 | 92 | 92 |
| Inlet air temperature [° C.] | 90 | 90 | 90 | 90 | 90 | 90 |
| Product end temperature [° C.] | 50-55 | 50-55 | 50-55 | 50-55 | 50-55 | 50-55 |

The granulates were mixed with flavour granulate and 0.50 per cent magnesium stearate by use of a Erweka tumbling mixer at 27 rpm for 5 minutes, batch size of approximately 5 kg.

Tablets were manufactured by use of a Korach PH106 instrumented rotary press and 14 mm round flat, bevelled edged punches. Target of tablet mass was adjusted to give an amount of 1250 mg calcium carbonate per tablet. Compression force was adjusted for crushing strengths of approximately 40 N, 70 N and 100 N for each granulate in order to achieve a crushing strength/comprssion force profile.

Composition of Tablets

| Composition | Experiment (1) | Experiment (2) | Experiment (3) | Experiment (4) | Experiment (5) | Experiment (6) |
|---|---|---|---|---|---|---|
| Calcium carbonate | 1250 | 1250 | 1250 | 1250 | 1250 | 1250 |
| Xylitol | 113.55 | 131.14 | 111.18 | 131.14 | 131.14 | 131.14 |
| PVP | 13.56 | 10.09 | 8.55 | 10.09 | 10.09 | 10.09 |
| Sucralose | 0.428 | 0.504 | 0.43 | 0.504 | 0.504 | 0.504 |
| Durarome flavour | 14 | 14 | 14 | 14 | 14 | 14 |
| Magnesium stearate | 7 | 7 | 7 | 7 | 7 | 7 |

The tablets are characterised by crushing strength, disintegration, slip time of hanging tablet.

Figure 9:
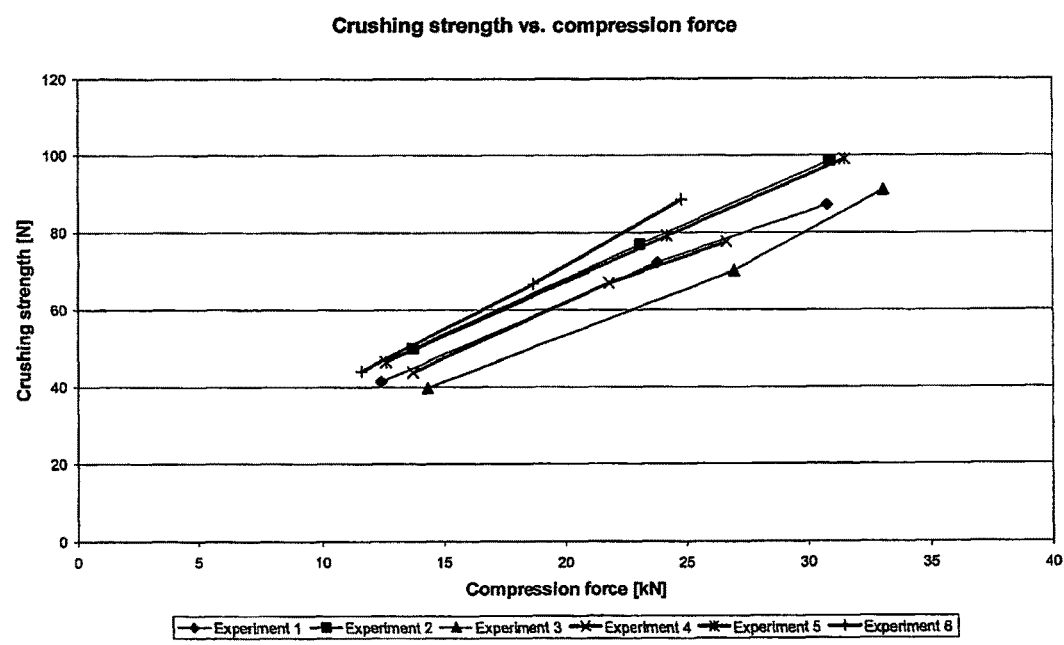
FIG. 9 illustrates the impact of tablet design on its crushing strength.
Figure 10:
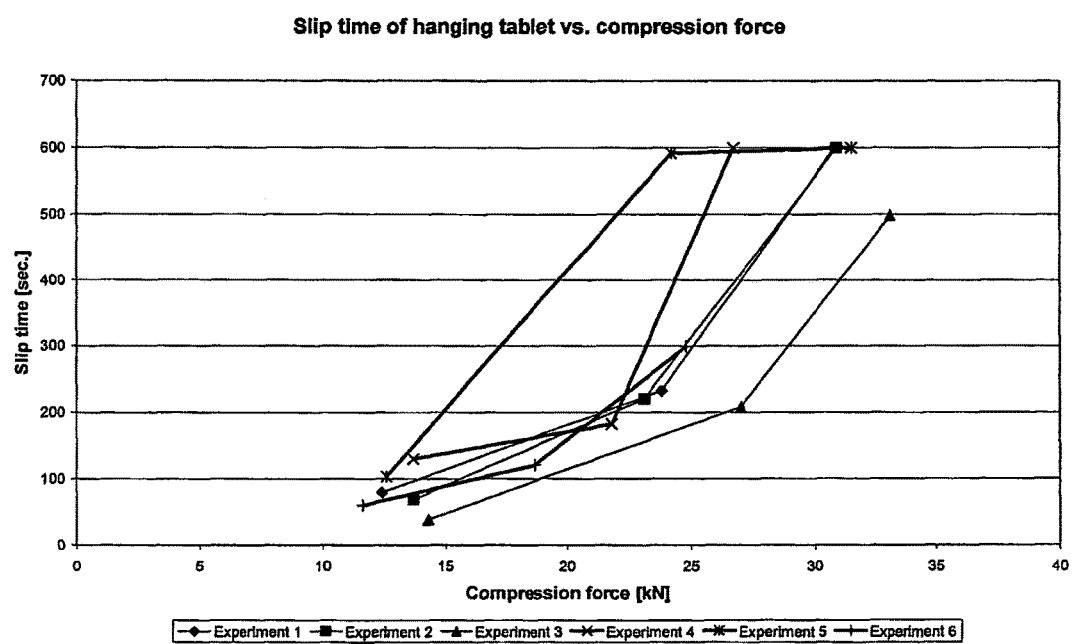
FIG. 10 illustrates the slip time of a hanging tablet.
Figure 11:
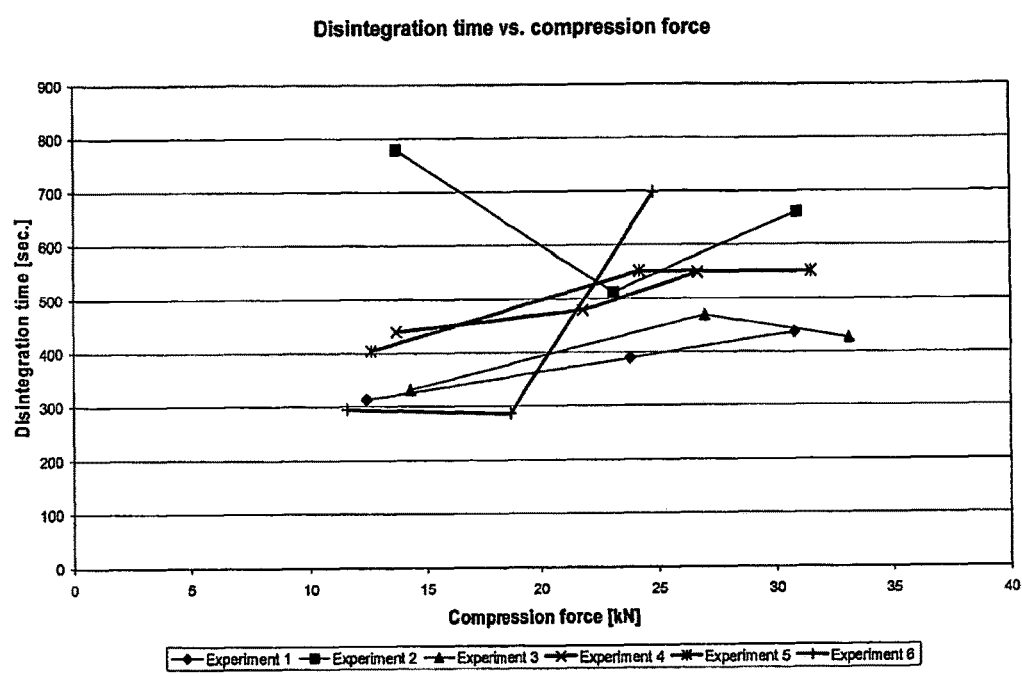
FIG. 11 illustrates the disintegration time for a tablet.

The impact on crushing strength of the design described above is shown in FIG. 9, slip time of a hanging tablet in FIG. 10 and disintegration time in FIG. 11. The robustness of the formulations is illustrated by comparison of the replications (test 4-6) with variation, test 1-3, in the amount of xylitol and PVP (compositions of tablets) and liquid flow rats and rpm (actual design).

The lack of major differences in crushing strength, alp time and disintegration time between tests 1-6 underlines the robustness of tablets based on the Schugi-Flex-O-Mix technology.

33C. Granulation in a Schugi Flexomix, Omitting Polymer in the Formulation

The manufacture and characterisation of tablets was performed as described in example 33C with the following test design and composition:

| Experiment | (8) |
|---|---|
| Powder mixture | |
| Calcium carbonate % | 100 |
| Xylitol % | — |
| Sorbitol % | — |
| PVP 30 % | — |
| Granulation liquid | |
| (water) | 39.91 |
| Xylitol % | 59.87 |
| PVP 30 % | — |
| Sucralose % | 0.22 |
| Sorbitol % | — |
| Schugi rpm | 4000 |
| Powder flow [kg/h] | 500 |
| Granulation liquid flow [kg/h] | 87 |
| Inlet air temperature [° C.] | 90 |
| Product end temperature [° C.] | 50-55 |

Composition of Tablets

| Composition | Experiment (8) |
|---|---|
| Calcium carbonate | 1250 |
| Xylitol | 130.22 |
| PVP | — |
| Sucralose | 0.47 |
| Durarome flavour | 14 |

-continued

| Composition | Experiment (8) |
|---|---|
| Magnesium stearate | 5 |

The compression experiment showed that it was not possible to obtain tablets of acceptble quality due to capping or the tablets being too soft.

Example 34

Illustration of Coated and Non-Coated Surfaces of a Calcium Containing Compound Granulated Using Xylitol as the Soluble Compound and PVP 30 as the Polymer in the Granulation Liquid Granulates manufactured according to example 29 was tested by XPS, see example 29 for results. It is recorded that between 20.9% and 26.9% of the visible surfaces of the calcium containing compound in the granulates are not coated by the dry matter constituents of the granulation liquid. ESEM (Environmental Scanning Electron Microscopy) was used to investigate the appearance of these non coated surfaces.

Figure 12A:
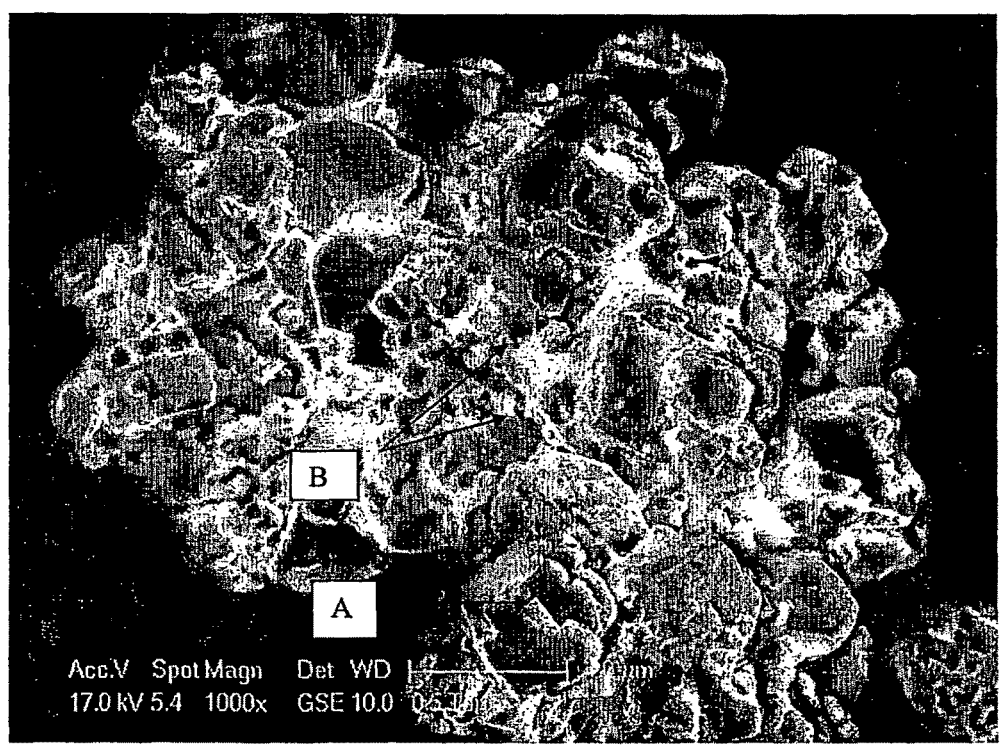
FIGS. 12A-12C illustrate ESEM (Environmental Scanning Electron Microscopy) images that were used to investigate the appearance of granulates manufactured according to example 29.
Figure 12B:
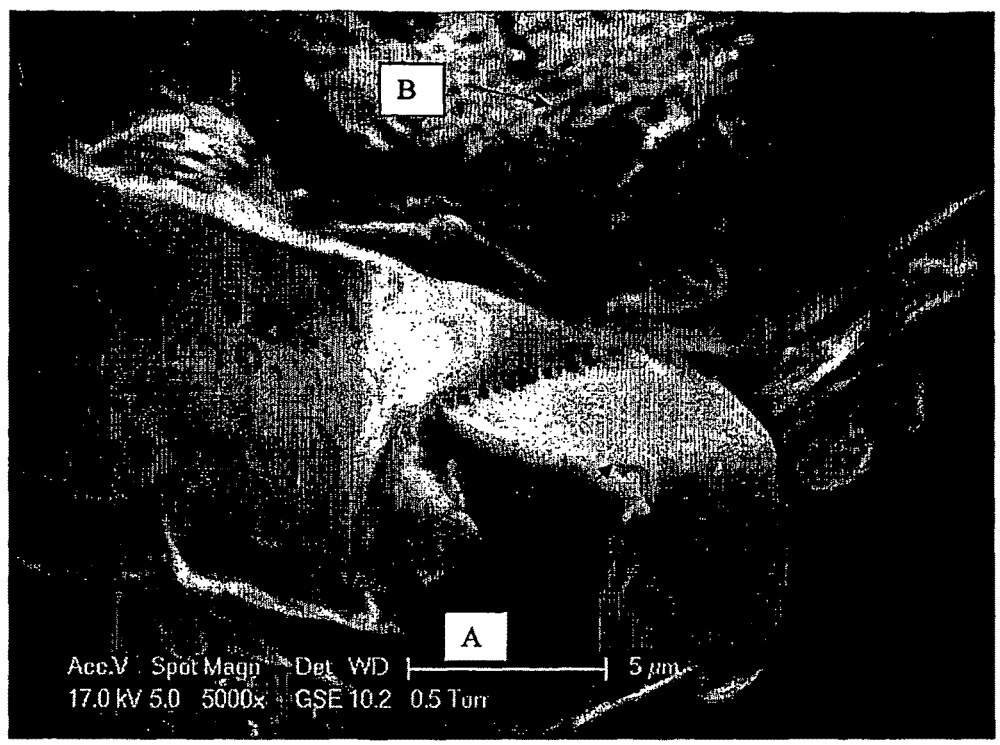
Figure 12C:
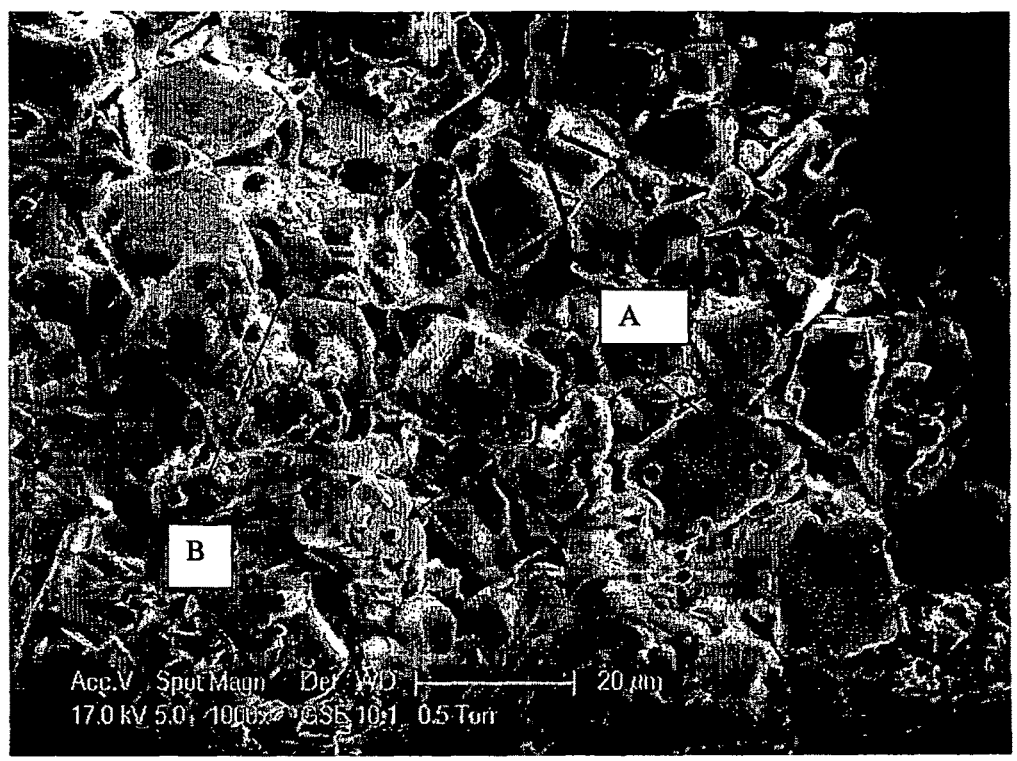

In FIG. 12a-12c arrows designated A are pointing at areas of non coated surface area of the calcium containing compound. These areas we often characterised by sharp edges or rather large flat areas or straight line-like patterns on the surface. Arrows designated B are pointing towards coated areas. These areas are characterised by rounded surfaces or wave like patterns or irregular areas.

In view of the results of Example 29, these results show that it is not necessary to have a 100% coating or coverage of the Ca-containing compound with the ingredients in the coating composition or the granulation liquid.

In the following examples are described further planned investigations.

Example 35

Wet Granulation in a Twin Screw Extruder

The compositions to be tested in this experiment are as follows

| Raw materials | Amounts in percent |
|---|---|
| Calcium carbonate | 50-95 |
| Water-soluble substance | 3-40 |
| Polymeric substance with binding properties | 0.5-5 |

-continued

| Raw materials | Amounts in percent |
| --- | --- |
| Flavor | 0.1-5 |
| Vitamin $D_3$ powder | 0.1-5.5 |
| Magnesium stearate | 0.2-2 |

Calcium carbonate is mixed with a part of the water-soluble substance and transferred to the starting section of a Leistritz twin screw extruder MIC 27GL/28D, 8.4 kW.

The mixture is wetted by adding to the extruder a solution/suspension of the rest of the water-soluble substance and the polymeric substance with binding properties.

The powder feed is set to 100 g/min and the screw speed 100 rpm

No die plate is required.

The granulated powder mass is transferred to a fluid bed dryer where it is dried to a water content below 1.0%.

The dried granulate is passed through a 1.5 mm screen and mixed with the remaining excipients to the final granulate.

The final granulate is compressed to chewable tablets.

Example 36

Hot Melt Granulation in a Twin Screw Extruder

The compositions to be tested in this experiment is a follows

| Raw materials | Amounts in percent |
| --- | --- |
| Calcium carbonate | 50-95 |
| Water-soluble substance | 3-40 |
| Polymeric substance with binding properties | 0.5-5 |
| Flavor | 0.1-5 |
| Vitamin $D_3$ powder | 0.1-5.5 |
| Magnesium stearate | 0.2-2 |

A mixture of the water-soluble substance and the polymeric substance with binding properties is transferred to the starting section of a Leistriz twin screw extruder MIC 27GL/28D, 8.4 kW with a temperature profile adjusted to the flowing:

| Temperature profile, segments; ° C. | | | | | | |
| --- | --- | --- | --- | --- | --- | --- |
| start | 2 | 3 | 4 | 5 | 6 | end |
| 60 | 120 | 120 | 120 | 120 | 120 | 100 |

The powder feed is adjusted to fit the actual formulation and the screw speed is fixed at 100 rpm.

Calcium carbonate is transferred to the twin screw extruder at section 3 The powder feed is set to 100 g/min No die plate is used.

The granulated powder mass is cooled down and afterwards the granulate is passed through a 1.5 mm screen and mixed with the remaining excipients to the final granulate. The final granulate is compressed to chewable tablets.

Example 37

Hot Melt Granulation in a Twin Screw Extruder

The compositions to be tested in this experiment are as follows

| Raw materials | Amounts in percent |
| --- | --- |
| Calcium carbonate | 50-95 |
| Water-soluble substance | 3-40 |
| Polymeric substance with binding properties | 0.5-5 |
| Flavor | 0.1-5 |
| Vitamin $D_3$ powder | 0.1-5.5 |
| Magnesium stearate | 0.2-2 |

A mixture of the soluble filer, the binding polymer and calcium carbonate is transferred to the starting section of a Leistritz twin screw extruder MIC 27GL/28D, 8.4 kW with a temperature profile adjusted to the following:

| Temperature profile, segments; ° C. | | | | | | |
| --- | --- | --- | --- | --- | --- | --- |
| start | 2 | 3 | 4 | 5 | 6 | end |
| 60 | 120 | 120 | 120 | 120 | 120 | 100 |

The powder feed is adjusted to fit the actual formulation and the screw speed is fixed at 100 rpm. No die plate is required.

The granulated powder mass is cooled down and afterwards the granulate is passed through a 1.5 mm screen and mixed with the remaining excipients to the final granulate.

The final granulate is compressed to chewable tablets.

Example 38

Hot Melt Granulation in a Twin Screw Extruder

The compositions to be tested in this experiment are as follows

| Raw materials | Amounts in percent |
| --- | --- |
| Calcium carbonate | 50-95 |
| Water-soluble substance | 3-40 |
| Polymeric substance with binding properties | 0.5-5 |
| Flavor | 0.1-5 |
| Vitamin $D_3$ powder | 0.1-5.5 |
| Magnesium stearate | 0.2-2 |

A mixture of the water-soluble substance and the polymeric substance with binding properties wetted with water and is then is transferred to the starting section of a Leistritz twin screw extruder MIC 27GL/28D, 8.4 kW with a temperature profile adjusted to the following:

| Temperature profile, segments; ° C. | | | | | | |
| --- | --- | --- | --- | --- | --- | --- |
| start | 2 | 3 | 4 | 5 | 6 | end |
| 60 | 120 | 120 | 120 | 120 | 120 | 100 |

The powder feed is adjusted to fit the actual formulation and the screw speed is fixed at 100 rpm.

Calcium carbonate is transferred to the twin screw extruder at section 3 The powder feed is set to 100 g/min No die plate is required.

The granulated powder mass is cooled down and afterwards the granulate is passed through a 1.5 mm screen and mixed with the remaining excipients to the final granulate. The final granulate is compressed to chewable tablets.

Example 39

Hot Melt Granulation in a Twin Screw Extruder

The compositions to be tested in this experiment are as follows

| Raw materials | Amounts in percent |
|---|---|
| Calcium carbonate | 50-95 |
| Water-soluble substance | 3-40 |
| Polymeric substance with binding properties | 0.5-5 |
| Flavor | 0.1-5 |
| Vitamin $D_3$ powder | 0.1-5.5 |
| Magnesium stearate | 0.2-2 |

A mixture of the water-soluble substance and the polymeric substance with binding properties wetted with water is mixed with calcium carbonate and then transferred to the starting section of a Leistritz twin screw extruder MIC 27GL/28D, 8.4 kW with a temperature profile adjusted to the following:

| Temperature profile, segments; °C. | | | | | | |
|---|---|---|---|---|---|---|
| start | 2 | 3 | 4 | 5 | 6 | end |
| 60 | 120 | 120 | 120 | 120 | 120 | 100 |

The powder feed is adjusted to fit the actual formulation and the screw speed is fixed at 100 rpm No die plate is required.

The granulated powder mass is cooled down and afterwards the granulate is passed through a 1.5 mm screen and mixed with the remaining excipients to the final granulate. The final granulate is compressed to chewable tablets.

Example 40

Granulation in a Spray Dryer

The compositions to be tested in this experiment are as follows

| Raw materials | Amounts in percent |
|---|---|
| Calcium carbonate | 50-95 |
| Water-soluble substance | 3-40 |
| Polymeric substance with binding properties | 0.5-5 |
| Flavor | 0.1-5 |
| Vitamin $D_3$ powder | 0.1-5.5 |
| Magnesium stearate | 0.2-2 |

The water-soluble substance is dissolved in a solvent, the polymeric substance with binding properties is dissolved/dispersed in the solution and finally the calcium carbonate is dispersed in the solution/dispersion, the final content of solids in the slurry is from 10% to 90%. Spraying is carried out using a nozzle introduced in a dry stream of air having a temperature between 120° C. and 300° C.

The resultant granulate is dried optionally by use of a fluid bed to a water content below 1.0%.

The dried granulate is passed through a 1.5 mm screen and mixed with the remaining excipients to the final granulate.

The final granulate is compressed to chewable tablets.

The invention claimed is:

1. A granulated calcium-containing compound, wherein the calcium-containing compound is in the form of particles and/or crystals that have been granulated with a granulating composition containing i) xylitol, and ii) one or more polymeric substances selected from the group consisting of povidones and copovidones, and mixtures thereof, wherein at least a part of the surface of the calcium-containing compound is provided with a film that is formed by the granulating composition, and wherein the xylitol constitutes from about 2% to about 20% of the total weight of the granulated calcium-containing compound, and the one or more polymeric substances constitutes from about 0.09% to about 10% of the total weight of the granulated calcium-containing compound.

2. The granulated calcium-containing compound according to claim 1, wherein at least about 50% of the surface area of the calcium-containing compound is covered with the film that is formed by the granulating composition.

3. The granulated calcium-containing compound according to claim 2, wherein the film is a continuous film.

4. The granulated calcium-containing compound according to claim 1, wherein the povidone is selected from the group consisting of povidone K-90, K-30, K-25, K-17, K-12, and mixtures thereof.

5. The granulated calcium-containing compound according to claim 1, wherein the calcium-containing compound is selected from the group consisting of calcium carbonate, calcium citrate, calcium lactate, calcium phosphate including tricalcium phosphate, calcium gluconate, bisglycino calcium, calcium citrate maleate, hydroxyapatite including solvates thereof, and mixtures thereof.

6. The granulated calcium-containing compound according to claim 1, wherein the calcium-containing compound is calcium carbonate.

7. The granulated calcium-containing compound according to claim 6, wherein the specific surface area of the calcium carbonate is from about 0.1 to about 3 $m^2/g$.

8. The granulated calcium-containing compound according to claim 6, wherein the specific surface area of the calcium carbonate is from about 0.1 to about 1.2 $m^2/g$.

9. The granulated calcium-containing compound according to claim 1, in combination with a vitamin.

10. The granulated calcium-containing compound according to claim 9, wherein the vitamin is selected from the group consisting of vitamin D, vitamin B, vitamin K, and derivatives thereof.

11. A composition comprising a granulated calcium-containing compound according to claim 1 and one or more pharmaceutically acceptable excipients.

12. The composition according to claim 11, which is in particulate form.

13. The composition according to claim 12 for use in the manufacture of a pharmaceutical or nutritional composition.

14. The composition according to claim 13, wherein the pharmaceutical or nutritional composition is in the form of tablets, capsules, pellets, beadlets, granules, granulates, or powders.

15. The composition according to claim 14, which is in the form of a tablet.

16. The composition according to claim 11, further comprising a vitamin.

17. The composition according to claim 16, wherein the vitamin is selected from the group consisting of vitamin D, vitamin B, vitamin K, and derivatives thereof.

* * * * *